United States Patent
Zhao

(10) Patent No.: US 12,082,953 B2
(45) Date of Patent: Sep. 10, 2024

(54) SYSTEMS AND METHODS FOR POSITIONING

(71) Applicant: SHANGHAI UNITED IMAGING HEALTHCARE CO., LTD., Shanghai (CN)

(72) Inventor: Xiaofen Zhao, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 236 days.

(21) Appl. No.: 17/446,835

(22) Filed: Sep. 3, 2021

(65) Prior Publication Data

US 2022/0061781 A1 Mar. 3, 2022

(30) Foreign Application Priority Data

Sep. 3, 2020 (CN) .......................... 202010916972.0

(51) Int. Cl.
*A61B 6/04* (2006.01)
*A61B 6/00* (2006.01)
(Continued)

(52) U.S. Cl.
CPC .......... *A61B 6/0487* (2020.08); *A61B 6/0407* (2013.01); *A61B 6/465* (2013.01); *A61B 6/467* (2013.01); *A61B 6/488* (2013.01); *A61B 6/54* (2013.01); *A61B 6/582* (2013.01); *G06F 3/0482* (2013.01); *G06F 3/04847* (2013.01);
(Continued)

(58) Field of Classification Search
CPC ......... A61B 5/70; A61B 5/704; A61B 6/0487; A61B 6/545; A61B 6/5247; A61B 6/488
See application file for complete search history.

(56) References Cited

U.S. PATENT DOCUMENTS

2004/0082852 A1* 4/2004 Cherek ................ A61B 6/0487
600/427
2004/0254456 A1* 12/2004 Ritter ..................... A61B 90/36
600/425
(Continued)

FOREIGN PATENT DOCUMENTS

CN 107789001 A 3/2018
CN 108013896 A 5/2018
(Continued)

OTHER PUBLICATIONS

First Office Action in Chinese Application No. 202010916972.0 mailed on Jun. 6, 2022, 20 pages.

*Primary Examiner* — Keith M Raymond
*Assistant Examiner* — Milton Truong
(74) *Attorney, Agent, or Firm* — METIS IP LLC

(57) ABSTRACT

Systems and methods for positioning in medical systems are provided. The system may obtain data associated with a scanning range of a subject. The system may also obtain an image of the subject on a couch of a medical radiation device. The image may be acquired by an imaging device when the couch is at a first position. The system may determine a position of the scanning range of the subject in the image. The system may further cause, based on the position of the scanning range in the image, the couch to move to a second position. The scanning range of the subject may be in a radiation region of the medical radiation device when the couch is located at the second position.

20 Claims, 9 Drawing Sheets

(51) Int. Cl.
    *A61B 6/46*     (2024.01)
    *A61B 6/58*     (2024.01)
    *G06F 3/0482*     (2013.01)
    *G06F 3/04847*     (2022.01)
    *G06T 7/00*     (2017.01)
    *G06T 7/50*     (2017.01)
    *G06T 7/70*     (2017.01)
    *A61B 5/055*     (2006.01)

(52) U.S. Cl.
    CPC .............. *G06T 7/0012* (2013.01); *G06T 7/50* (2017.01); *G06T 7/70* (2017.01); *A61B 5/055* (2013.01); *G06T 2200/24* (2013.01); *G06T 2207/30004* (2013.01); *G06T 2207/30196* (2013.01)

(56) References Cited

U.S. PATENT DOCUMENTS

| | | | | |
|---|---|---|---|---|
| 2005/0085710 A1* | 4/2005 | Earnst | ................... | A61B 6/0487 378/65 |
| 2005/0234327 A1* | 10/2005 | Saracen | ................. | A61B 6/548 600/407 |
| 2007/0211844 A1 | 9/2007 | Shi et al. | | |
| 2008/0064952 A1* | 3/2008 | Li | ............................ | A61B 5/06 600/424 |
| 2008/0123924 A1* | 5/2008 | Nabatame | ............ | A61B 6/0487 382/131 |
| 2010/0059679 A1* | 3/2010 | Albrecht | ................ | H04N 7/181 250/363.04 |
| 2015/0119703 A1 | 4/2015 | Mitchell et al. | | |
| 2017/0189719 A1* | 7/2017 | Liu | ....................... | A61N 5/1081 |
| 2018/0107226 A1* | 4/2018 | Yang | .................... | G08G 5/0069 |
| 2018/0184997 A1* | 7/2018 | Tsukagoshi | ............. | A61B 6/469 |
| 2018/0284594 A1* | 10/2018 | Gao | ...................... | A61B 6/0487 |
| 2019/0076050 A1* | 3/2019 | Keil | ....................... | G01R 33/543 |
| 2020/0258243 A1* | 8/2020 | Chang | .................... | A61B 5/107 |
| 2020/0323496 A1* | 10/2020 | Eibenberger | ......... | A61B 6/0487 |

FOREIGN PATENT DOCUMENTS

| | | |
|---|---|---|
| CN | 108294772 A | 7/2018 |
| CN | 109171789 A | 1/2019 |
| CN | 109363872 A | 2/2019 |
| CN | 109924993 A | 6/2019 |
| CN | 111407301 A | 7/2020 |
| CN | 111493909 A | 8/2020 |
| CN | 107468266 B | 3/2021 |

* cited by examiner

700

```
┌─────────────────────────────────────────────────────────────┐     710
│ Obtaining a transforming relationship between a first       │╲╱
│ coordinate system applied to an image and a second          │
│ coordinate system                                           │
└─────────────────────────────────────────────────────────────┘
                              │
                              ▼
┌─────────────────────────────────────────────────────────────┐     720
│ Determining, based on a position of the reference range in  │╲╱
│ the image and the transforming relationship, a starting     │
│ position of a scanning range and an ending position of the  │
│ scanning range in the second coordinate system              │
└─────────────────────────────────────────────────────────────┘
                              │
                              ▼
┌─────────────────────────────────────────────────────────────┐     730
│ Determining, based on the starting position of the scanning │╲╱
│ range in the second coordinate system and a position of the │
│ radiation region in the second coordinate system, a first   │
│ distance                                                    │
└─────────────────────────────────────────────────────────────┘
                              │
                              ▼
┌─────────────────────────────────────────────────────────────┐     740
│ Determining, based on the ending position of the scanning   │╲╱
│ range in the second coordinate system and the position of   │
│ the radiation region in the second coordinate system, a     │
│ second distance                                             │
└─────────────────────────────────────────────────────────────┘
                              │
                              ▼
┌─────────────────────────────────────────────────────────────┐     750
│ Determining, based on the first position, the first         │╲╱
│ distance, and the second distance, a second position of     │
│ the couch                                                   │
└─────────────────────────────────────────────────────────────┘
```

FIG. 7

SYSTEMS AND METHODS FOR POSITIONING

CROSS-REFERENCE TO RELATED APPLICATIONS

This application claims priority of Chinese Patent Application No. 202010916972.0, filed on Sep. 3, 2020, the contents of which are hereby incorporated by reference.

TECHNICAL FIELD

This disclosure generally relates to a medical system, and more particularly, relates to systems and methods for positioning in the medical system.

BACKGROUND

Medical systems, such as a computed tomography (CT) system, a magnetic resonance imaging (MRI) system, a positron emission tomography (PET) system, a radiotherapy (RT) system, etc., are widely used in disease diagnosis and/or treatment for various medical conditions (e.g., tumors, coronary heart diseases, or brain disease). Conventionally, before an object (e.g., a patient or a portion thereof) is performed a medical procedure (e.g., observation, treatment), with the assistance of a user (e.g., a doctor, a radiologist, a nurse), the object may be placed on a table in the required posture and moved to a position in a detection region manually by an operator according to experience, which decreases the accuracy and efficiency of positioning, thereby decreasing the quality of the medical procedure.

Therefore, it is desirable to provide effective systems or methods for positioning in the medical system.

SUMMARY

An aspect of the present disclosure relates to a system for positioning in a medical system. The system may include at least one storage device and at least one processor. The at least one storage device may include a set of instructions. The at least one processor may be in communication with the at least one storage device. When executing the set of instructions, the at least one processor may be directed to perform operations. The operations may include obtaining data associated with a scanning range of a subject. The operations may also include obtaining an image of the subject on a couch of a medical radiation device. The image may be acquired by an imaging device when the couch is at a first position. The operations may include determining a position of the scanning range of the subject in the image. The operations may further include causing, based on the position of the scanning range in the image, the couch to move to a second position. The scanning range of the subject may be in a radiation region of the medical radiation device when the couch is located at the second position.

In some embodiments, the obtaining data associated with the scanning range of the subject may include obtaining the data associated with the scanning range of the subject from a scanning plan; or obtaining the data associated with the scanning range of the subject according to an input of a user. The data associated with the scanning range of the subject may include a starting position corresponding to a first anatomical location of the subject and an ending position corresponding to a second anatomical location of the subject.

In some embodiments, the obtaining data associated with the scanning range of the subject may include causing a display device to present a user interface including multiple operating controls; and determining the data associated with the scanning range of the subject in response to receiving an input of the user through the multiple operating controls.

In some embodiments, the user interface may be used to configure a scanning protocol, and include a human anatomical structure map that includes multiple anatomical locations each of which corresponds to one of the multiple operating controls. The determining the data associated with the scanning range of the subject in response to receiving an input of the user through the multiple operating controls may include receiving an operation of the user on one or more of the multiple operating controls; determining, based on the operation of the user on one or more of the multiple operating controls, a configuration of the scanning range in the scanning protocol; and determining, based on the configuration of the scanning range, the data associated with the scanning range of the subject.

In some embodiments, the image may be acquired from an overlook view of the subject by the imaging device that is located above the couch.

In some embodiments, the determining a position of the scanning range of the subject in the image may include determining, based on the data associated with the scanning range, the position of the scanning range of the subject in the image using a trained machine learning model.

In some embodiments, the causing, based on the position of the scanning range in the image, the couch to move to a second position may include determining, based on the position of the reference range in the image, at least one of a first distance between a starting position of the scanning range and the radiation region or a second distance between an ending position of the scanning range and the radiation region when the couch is at the first position; and causing, based on at least one of the first distance or the second distance, the couch to move to the second position.

In some embodiments, the determining, based on the position of the reference range in the image, a first distance between a starting position of the scanning range and the radiation region when the couch is at the first position and a second distance between an ending position of the scanning range and the radiation region when the couch is at the first position may include obtaining a transforming relationship between a first coordinate system applied to the image and a second coordinate system; determining, based on the position of the reference range in the image and the transforming relationship, the starting position of the scanning range and the ending position of the scanning range in the second coordinate system; determining, based on the starting position of the scanning range in the second coordinate system, and a position of the radiation region in the second coordinate system, the first distance; and determining, based on the ending position of the scanning range in the second coordinate system, and the position of the radiation region in the second coordinate system, the second distance.

In some embodiments, the causing, based on the first distance and the second distance, the couch to move to the second position may include determining, based on the depth information, a body thickness of the subject; determining, based on the first distance and the second distance, the second position of the couch in a horizontal plane parallel to the couch; determining, based on the body thickness of the subject, the second position of the couch in a vertical direction perpendicular to the horizontal plane; and causing the couch to move to the second position.

In some embodiments, the control platform may be configured to obtaining multiple calibration images of the couch acquired by the imaging device, each of the calibration images corresponding to a spatial position of the couch in the second coordinate system; and determining, based on the multiple calibration images of the couch and the spatial position, the transforming relationship.

In some embodiments, the operations may further include outputting, through a user interface, the second position to a terminal of a user; receiving an adjustment instruction for adjusting the second position provided by the user through the user interface; and causing, based on the adjustment instruction, the couch to move.

Another aspect of the present disclosure relates to a method for positioning in a medical system. The method may include obtaining data associated with a scanning range of a subject. The method may also include obtaining an image of the subject on a couch of a medical radiation device. The image may be acquired by an imaging device when the couch is at a first position. The method may include determining a position of the scanning range of the subject in the image. The method may further include causing, based on the position of the scanning range in the image, the couch to move to a second position. The scanning range of the subject may be in a radiation region of the medical radiation device when the couch is located at the second position.

In some embodiments, the obtaining data associated with the scanning range of the subject may include obtaining the data associated with the scanning range of the subject from a scanning plan; or obtaining the data associated with the scanning range of the subject according to an input of a user. The data associated with the scanning range of the subject may include a starting position corresponding to a first anatomical location of the subject and an ending position corresponding to a second anatomical location of the subject.

In some embodiments, the obtaining data associated with the scanning range of the subject may include causing a display device to present a user interface including multiple operating controls; and determining the data associated with the scanning range of the subject in response to receiving an input of the user through the multiple operating controls.

In some embodiments, the user interface may be used to configure a scanning protocol, and include a human anatomical structure map that includes multiple anatomical locations each of which corresponds to one of the multiple operating controls. The determining the data associated with the scanning range of the subject in response to receiving an input of the user through the multiple operating controls may include receiving an operation of the user on one or more of the multiple operating controls; determining, based on the operation of the user on one or more of the multiple operating controls, a configuration of the scanning range in the scanning protocol; and determining, based on the configuration of the scanning range, the data associated with the scanning range of the subject.

In some embodiments, the causing, based on the position of the scanning range in the image, the couch to move to a second position may include determining, based on the position of the reference range in the image, at least one of a first distance between a starting position of the scanning range and the radiation region or a second distance between an ending position of the scanning range and the radiation region when the couch is at the first position; and causing, based on at least one of the first distance or the second distance, the couch to move to the second position.

In some embodiments, the determining, based on the position of the reference range in the image, a first distance between a starting position of the scanning range and the radiation region when the couch is at the first position and a second distance between an ending position of the scanning range and the radiation region when the couch is at the first position may include obtaining a transforming relationship between a first coordinate system applied to the image and a second coordinate system; determining, based on the position of the reference range in the image and the transforming relationship, the starting position of the scanning range and the ending position of the scanning range in the second coordinate system; determining, based on the starting position of the scanning range in the second coordinate system, and a position of the radiation region in the second coordinate system, the first distance; and determining, based on the ending position of the scanning range in the second coordinate system, and the position of the radiation region in the second coordinate system, the second distance.

In some embodiments, the causing, based on the first distance and the second distance, the couch to move to the second position may include determining, based on the depth information, a body thickness of the subject; determining, based on the first distance and the second distance, the second position of the couch in a horizontal plane parallel to the couch; determining, based on the body thickness of the subject, the second position of the couch in a vertical direction perpendicular to the horizontal plane; and causing the couch to move to the second position.

In some embodiments, the method may further include outputting, through a user interface, the second position to a terminal of a user; receiving an adjustment instruction for adjusting the second position provided by the user through the user interface; and causing, based on the adjustment instruction, the couch to move.

Still another aspect of the present disclosure relates to a non-transitory computer readable medium. The non-transitory computer readable medium may include executable instructions that, when executed by at least one processor, direct the at least one processor to perform a method for positioning in a medical system. The method may include obtaining data associated with a scanning range of a subject. The method may also include obtaining an image of the subject on a couch of a medical radiation device. The image may be acquired by an imaging device when the couch is at a first position. The method may include determining a position of the scanning range of the subject in the image. The method may further include causing, based on the position of the scanning range in the image, the couch to move to a second position. The scanning range of the subject may be in a radiation region of the medical radiation device when the couch is located at the second position.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 7 is a flowchart illustrating an exemplary process for determining a second position of a couch according to some embodiments of the present disclosure;

DETAILED DESCRIPTION

Figure 1:
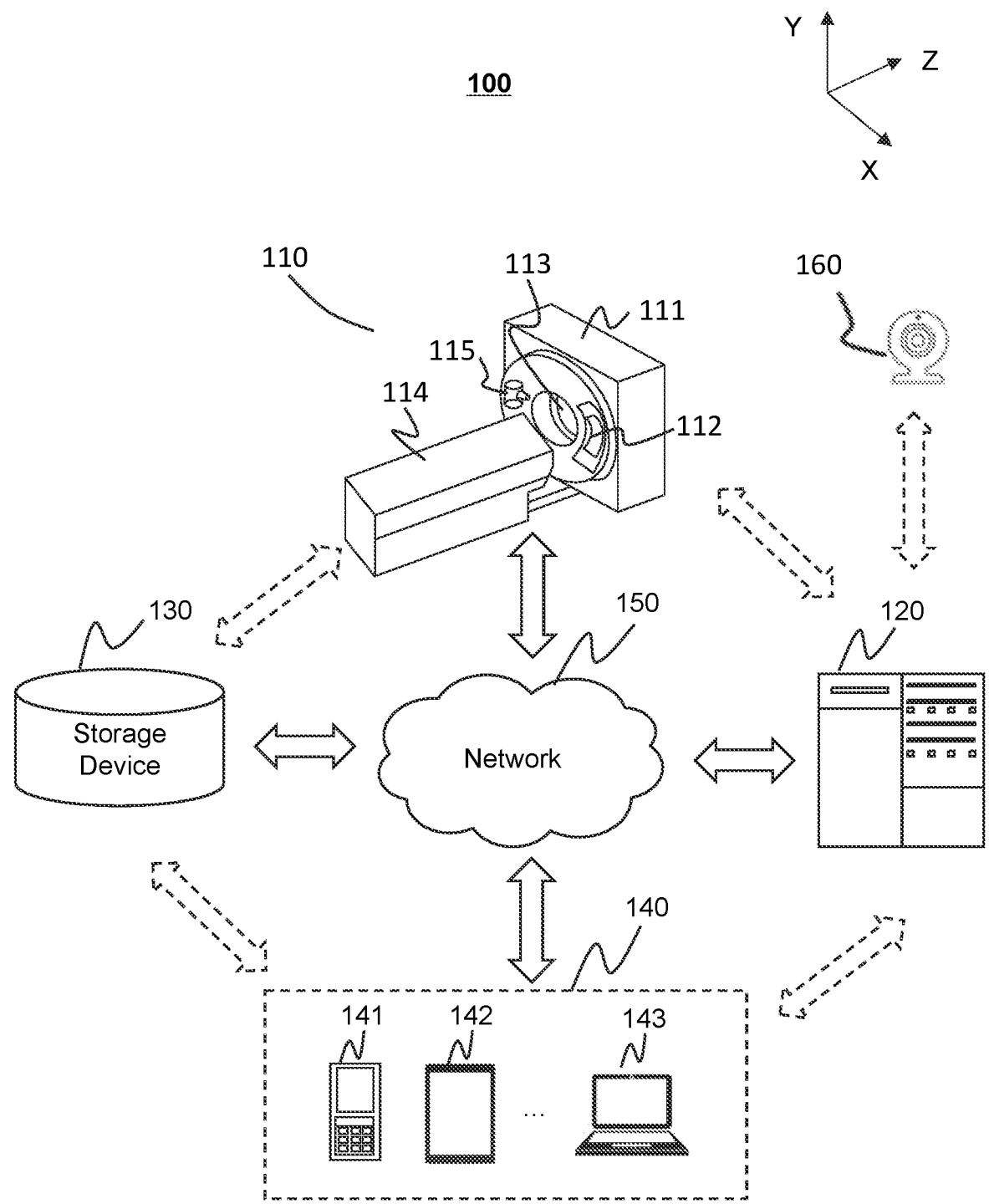
FIG. 1 is a schematic diagram illustrating an exemplary medical system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. Also, the term "exemplary" is intended to refer to an example or illustration.

It will be understood that the terms "system," "engine," "unit," "module," and/or "block" used herein are one method to distinguish different components, elements, parts, sections or assembly of different levels in ascending order. However, the terms may be displaced by another expression if they achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that, although the terms "first," "second," "third," etc., may be used herein to describe various elements, these elements should not be limited by these terms. These terms are only used to distinguish one element from another. For example, a first element could be termed a second element, and, similarly, a second element could be termed a first element, without departing from the scope of exemplary embodiments of the present disclosure.

The term "pixel" and "voxel" in the present disclosure are used interchangeably to refer to an element in an image. The term "image" in the present disclosure is used to refer to images of various forms, including a 2-dimensional image, a 3-dimensional image, a 4-dimensional image, etc.

Spatial and functional relationships between elements are described using various terms, including "connected," "attached," and "mounted." Unless explicitly described as being "direct," when a relationship between first and second elements is described in the present disclosure, that relationship includes a direct relationship where no other intervening elements are present between the first and second elements, and also an indirect relationship where one or more intervening elements are present (either spatially or functionally) between the first and second elements. In contrast, when an element is referred to as being "directly" connected, attached, or positioned to another element, there are no intervening elements present. Other words used to describe the relationship between elements should be interpreted in a like fashion (e.g., "between," versus "directly between," "adjacent," versus "directly adjacent," etc.).

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood the operations of the flowcharts may be implemented not in order. Conversely, the operations may be implemented in inverted order, or simultaneously. Moreover, one or more other operations may be added to the flowcharts. One or more operations may be removed from the flowcharts.

Moreover, while the systems and methods disclosed in the present disclosure are described primarily regarding position determination in a computed tomography (CT) system. It should be understood that this is only for illustration purposes. The systems and methods of the present disclosure may be applied to any other kind of medical system. In some embodiments, the medical system may include a single modality system and/or a multi-modality system. The single modality system may include, for example, a magnetic resonance imaging (MRI) system, a positron emission tomography (PET) system, a CT system, a single-photon emission computed tomography (SPECT) device, a radiotherapy (RT) device, or the like. The multi-modality system may include, for example, an MRI-CT system, a PET-MRI system, a SPECT-MRI system, a digital subtraction angiography (DSA)-MRI system, a PET-CT system, or the like.

The present disclosure relates to a system and method for positioning in the medical system with improved efficiency and accuracy. The system may obtain data associated with a scanning range of a subject and an image of the subject on a couch of a medical radiation device. The image may be acquired by an imaging device when the couch is at a first position. The system may determine a position of the scanning range of the subject in the image. The system may also cause, based on the position of the scanning range in the image, the couch to move to a second position, such that the scanning range of the subject may be located in a radiation region of the medical radiation device. For example, the center of the scanning range may coincide with the isocenter of the medical radiation device when the couch is moved to the second position. In some embodiments, the system may determine a moving distance of the couch from the first position to the second position based on the position of the scanning range in the image and the position of the radiation region. In some embodiments, the system may determine the second position of the couch based on the position of the scanning range in the image. According to some embodiments, the scanning range of the subject may be automatically determined from the image, and the couch may be controlled to move a distance or to the second position that is determined based on the position of the scanning range of the subject in the image, such that the scanning range of the subject is moved to a desired position in the radiation region for receiving radiation, which may be independent on the experience and determination of an operator of the medical procedure. Therefore, the efficiency and accuracy of the positioning may be improved. In addition, the present disclosure provides a user interface for positioning, such as adjusting or determining the scanning range by an operator, which may reduce operation difficulty.

FIG. 1 is a schematic diagram illustrating an exemplary medical system according to some embodiments of the present disclosure. As illustrated, a medical system 100 may include a medical radiation device 110, a processing device 120, a storage device 130, a terminal 140, a network 150, and an imaging device 160. The components of the medical system 100 may be connected in one or more of various ways. Merely by way of example, as illustrated in FIG. 1, the medical radiation device 110 may be connected to the processing device 120 directly as indicated by the bi-directional arrow in dotted lines linking the medical radiation device 110 and the processing device 120, or through the network 150. As another example, the storage device 130 may be connected to the medical radiation device 110 directly as indicated by the bi-directional arrow in dotted lines linking the medical radiation device 110 and the storage device 130, or through the network 150. As still another example, the terminal 140 may be connected to the processing device 120 directly as indicated by the bi-directional arrow in dotted lines linking the terminal 140 and the processing device 120, or through the network 150.

The medical radiation device 110 may generate or provide image data by scanning a subject or at least a part of the subject and/or perform a treatment (e.g., radiotherapy) on the at least one part of the subject. In some embodiments, the medical radiation device 110 may include a single-modality device. The single-modality device may include, for example, an MRI device, a CT device, a PET device, an X-ray imaging device, a radiation therapy or radiotherapy (RT) device, or the like. In some embodiments, the medical radiation device 110 may include a multi-modality device. The multi-modality scanner may include a PET-CT device, a PET-MRI device, a CT-MRI device, or the like. The multi-modality scanner may perform multi-modality imaging simultaneously. For example, the PET-CT device may generate structural X-ray CT image data and functional PET image data simultaneously in a single scan. The PET-MRI device may generate MRI data and PET data simultaneously in a single scan. In some embodiments, the medical radiation device 110 may include an image-guided radiotherapy (IGRT) device. For example, the IGRT device may include a PET-RT device, or an MRI-RT device, etc.

Merely by way of example, the medical radiation device 110 may be a medical imaging device configured to scan a subject (or a part of the subject) to acquire image data. In some embodiments, the medical radiation device 110 may include a gantry 111, a detector 112, a couch 114, and a radioactive source 115. The gantry 111 may include a radiation region 113. The subject may be placed on the couch 114 and moved into the radiation region 113 to be scanned. The gantry 111 may support the detector 112 and the radioactive source 115. In some embodiments, the gantry 111 may be caused to rotate. For example, in a CT imaging device, the gantry 111 may be caused to rotate clockwise or counterclockwise around an axis (i.e., long axis) of the gantry 111. The scanning source 115 and the detector 112 may be caused to rotate with the gantry 111. The radioactive source 115 may emit radioactive rays to the subject. The radioactive rays may include a particle ray, a photon ray, or the like, or a combination thereof. In some embodiments, the radioactive rays may include a plurality of radiation particles (e.g., neutrons, protons, electron, μ-mesons, heavy ions), a plurality of radiation photons (e.g., X-ray, a γ-ray, ultraviolet, laser), or the like, or a combination thereof. The detector 112 may detect radiations and/or radiation events (e.g., gamma photons) emitted from the radiation region 113. In some embodiments, the detector 112 may include a plurality of detector units. A detector unit may include a scintillation detector (e.g., a cesium iodide detector) or a gas detector. The detector unit may be/include a single-row detector or a multi-rows detector. For example, in a PET imaging device, the detector 112 may detect a radiation beam (e.g., gamma photons) emitted from a subject located in the radiation region 113. After receiving the radiation beam emitted by the subject, the detector 112 may convert the emitted radiation beam into visible light, and then converted the visible light into electrical signals through a photoelectric conversion. The electrical signals may be converted into digital information by an analog/digital converter. The digital information may be input to a computing device (e.g., the processing device 120, a computer) for processing, or transmitted to a storage device (e.g., the storage device 130) for storage. In some embodiments, the medical radiation device 110 may be an MRI device. The MRI device may include a magnetic assembly, a radio frequency (RF) transmitting coil and/or an RF receiving coil (not shown in FIG. 1). The magnetic assembly may mainly include a main magnet configured to generate a main magnetic field BO and a gradient component configured to a gradient magnetic field. An RF pulse may be applied to the subject through the RF transmitting coil. Hydrogen protons in the subject may be excited to generate MR signals under the main magnetic field BO and the gradient magnetic field. The MR signals may be received through the RF receiving coil to generate a medical image.

In some embodiments, the couch 114 may be movably disposed in front of the radiation region 113 and a surface where the subject is located may be substantially parallel to the ground. The couch 114 may be caused to move in and out of the radiation region 113 (also referred to as a scanning region or detection region) by moving along an axial direction (e.g., a length direction or longitudinal direction) of the couch 114 (also referred to as a direction parallel to a Z-axis of the medical radiation device 110 as shown in FIG. 1). In some embodiments, the couch 114 may also be caused to move up and down in a direction (e.g., a vertical direction) perpendicular to the ground. The moving of the couch 114 in the vertical direction may cause a center of the scanning range of the subject may coincide with the isocenter of the medical radiation device in the vertical direction (also referred to as a direction parallel to a Y-axis of the medical radiation device 110 as shown in FIG. 1).

The subject may be biological or non-biological. For example, the subject may include a patient, a man-made subject, etc. As another example, the subject may include a specific portion, an organ, and/or tissue of the patient. Specifically, the subject may include the head, the neck, the thorax, the heart, the stomach, a blood vessel, soft tissue, a tumor, or the like, or any combination thereof. In some embodiments the subject may be a target subject as described elsewhere in the present disclosure.

The imaging device 160 may be configured to acquire image data of a scene in a radiation room where the medical radiation device 110 is located. For example, the imaging device 160 may acquire an image of the subject on the couch 114 of the medical radiation device 110. As another example, the imaging device 160 may acquire an image representing the subject and at least a portion (e.g., a portion that is close to the couch 114, i.e., a front end) of the medical radiation device 110. The image may include a static image, a video, an image sequence including multiple static images, etc. The visual sensors may capture image data representing different parts of the medical radiation device 110 from different perspectives. For example, the image may be acquired from an overlooking view of the subject by the imaging device 160. In some embodiments, the imaging device 160 may include one or more visual sensors, one or more thermal imaging sensors, one or more radars, etc. The visual sensors may refer to an apparatus for visual recording. The visual sensors may capture the image of the subject on the couch 114 of the medical radiation device 110. In some embodiments, the visual sensors may include a stereo camera configured to capture a static image or video. The stereo camera may include a binocular vision device or a multi-camera. In some embodiments, the visual sensors may include a three-dimensional (3D) camera. The 3D camera may acquire a 3D image of the subject. In some embodiments, the visual sensors may include a depth camera. The depth camera may acquire depth information of the subject. The thermal imaging sensor may refer to a device that captures an image using infrared radiation (IR). The image captured by the thermal imaging sensor may include temperature information and/or position information of the subject. Exemplary thermal imaging sensors may include a thermal imaging camera, a thermal imaging DVR, or the like, or any combination thereof. The radar may be configured to acquire radar echo data from the subject. The radar echo data may include data related to a motion of the subject. In some embodiments, the imaging device 160 may transmit the acquired image to the processing device 120, the storage device 130, and/or the terminal(s) 140 via the network 150. In some embodiments, the visual sensors may be located at different positions. For example, the imaging device 160 may be fixed on the gantry 111 through a connection structure (e.g., a mechanical connection, a welding connection, a bonging connection, etc.). As another example, the imaging device 160 may be disposed on a ceiling above the couch 114 through a connection structure (e.g., a mounting column arranged on the ground, etc.). The field view of each of at least a portion of the visual sensors may include at least a portion of the medical radiation device 110 and/or at least a portion of the couch. In some embodiments, the imaging device 160 may be rotated within an angle range to obtain images of the subject from different perspectives. In some embodiments, the imaging device 160 may be integrated into the medical radiation device 110.

In some embodiments, an image acquired by the imaging device 160 may apply a first coordinate system. The medical radiation device 110 may apply a second coordinate system. The first coordinate system (also referred to as image coordinate system) may be used to denote positions of pixels in the image. The second coordinate system may be used to denote a spatial position (e.g., spatial positions of different parts of the subject, the spatial positions of different parts of the medical radiation device 110 in the radiation room). The second coordinate system may be a spatial coordinate system. For example, the second coordinate system may be determined based on the medical radiation device 110. For example, a scanning center point (i.e., isocenter) of the detection region 113 may be determined as an origin of the second coordinate system. A long axis of the medical radiation device 110 may be determined as a Z-axis. A plane defined by an X-axis and a Y-axis of the second coordinate system may be perpendicular to the Z-axis. In some embodiments, a short axis of the couch 114 may be determined as the X-axis. A direction perpendicular to a plane defined by the X-axis and the Z-axis may be determined as a Y-axis. The scanning center point (i.e., isocenter) of the detection region 113 may include a center of rotation of the radioactive scanning source 115, a center of rotation of the detector 112, a geometric center of the gantry 111 (e.g., a circular center of the gantry 111), etc. In some embodiments, the couch 114 may be caused to move along the X-axis, the Y-axis, and/or the Z-axis. For example, the couch 114 may be moved in and out of the radiation region 113 along the Z direction, and adjusted along the Y-axis and/or the X-axis to adjust the distance between the couch 114 and the scanning center point.

A transforming relationship between the first coordinate system applied to the image and the second coordinate system may be used to perform a transform between characteristic information of a subject represented in the image (i.e., denoted by the first coordinate system) to characteristic information of the subject in the space (i.e., denoted by the second coordinate system). The characteristic information may include a position, a size (e.g., an area, a length, a width, a thickness, etc.). For example, the transforming relationship between the first coordinate system applied to the image and the second coordinate system may be used to transform a position of a part of the subject in the image to a position of the part of the subject in the space. As another example, the transforming relationship between the first coordinate system applied to the image and the second coordinate system may be used to transform a distance between a part (e.g., a first anatomical location, a second anatomical location) of the subject in the image and a reference position (e.g., the couch, a center, a boundary of the radiation region) to a distance between to the part of the subject in the image and the reference position in the space.

The processing device 120 may process data and/or information obtained from the medical radiation device 110, the storage device 130, the terminal(s) 140, and/or the imaging device 160. For example, the processing device 120 may obtain data associated with a scanning range of a subject. The processing device 120 may also obtain an image of the subject on the couch 114 of the medical radiation device 110. The image may be acquired by the imaging device 160 when the couch 114 is at a first position. The processing device 120 may determine a position of the scanning range of the subject in the image. The processing device 120 may further determine, based on the position of the scanning range in the image, a second position of the couch 114. The processing device 120 may cause the couch 114 to move to the second position. The scanning range of the subject may be in the detection region 113 of the medical radiation device 110 when the couch 114 is located at the second position.

In some embodiments, the first position and the second position may refer to spatial positions of the couch in the space. In some embodiments, a spatial position of the couch 114 in the space may be denoted by a couch code. In some embodiments, a point on the couch 114 (e.g., a central point of the couch 114, a point on a front end of the couch 114, a point on a rear end of the couch 114, etc.) may be determined as a reference point of the couch 114. The front end of the couch 114 refers to an end close to the medical radiation device 110. The rear end of the couch 114 refers to an end away from the medical radiation device 110. Coordinates of the reference point of the couch 114 in the second coordinate system may be determined as the couch code. That is, the couch code may be represented by three-dimensional coordinates. For example, if the reference point is the central point of the couch 114, the scanning center point of the radiation region 113 is determined as the origin of the second coordinate system, a direction toward the inside of the medical radiation device 110 along the long axis of the radiation region is determined as a direction of the Z-axis, and a vertical upward direction is determined as a direction of the Y-axis, a couch code (0, 20, 100) may indicate the reference point of the couch 114 is located 100 centimeters from the origin of the second coordinate system along the Z-axis and 20 centimeters higher than the origin of the second coordinate system along the Y-axis. In some embodiments, the couch code of the couch 114 may refer to a scale marked along the long axis of the couch 114 (e.g., the Z-axis). For example, the couch code may be marked with the scale gradually increasing from the front end of the couch to the rear end of the couch. Alternatively, the couch code may be marked with the scale gradually increasing from the rear end of the couch to the front end of the couch. As another example, if a length of the couch is 2 meters, the couch code of the couch 114 may be marked from 0 millimeters to 2000 millimeters according to a millimeter interval from the front end of the couch to the rear end of the couch.

The processing device 120 may determine a current couch code of the couch 114 at the first position based on the second coordinate system and the image of the subject during the movement of the couch 114 entering the cavity of the gantry. In some embodiments, the processing device 120 may display the current couch code in real time.

In some embodiments, the processing device 120 may be a single server or a server group. The server group may be centralized or distributed. In some embodiments, the processing device 120 may be local or remote. For example, the processing device 120 may access information and/or data from the medical radiation device 110, the storage device 130, the terminal(s) 140, and/or the imaging device 160 via the network 150. As another example, the processing device 120 may be directly connected to the medical radiation device 110, the terminal(s) 140, the imaging device 160, and/or the storage device 130 to access information and/or data. In some embodiments, the processing device 120 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 120 may be part of the terminal 140. In some embodiments, the processing device 120 may be part of the medical radiation device 110.

The storage device 130 may store data, instructions, and/or any other information. In some embodiments, the storage device 130 may store data obtained from the medical radiation device 110, the processing device 120, and/or the terminal(s) 140. The data may include image data acquired by the processing device 120, algorithms and/or models for processing the image data, etc. For example, the storage device 130 may store a scanning plan from the medical radiation device 110, scanning data from the medical radiation device 110, the image of the subject from the imaging device 160, etc. In some embodiments, the storage device 130 may store data and/or instructions that the processing device 120 and/or the terminal 140 may execute or use to perform exemplary methods described in the present disclosure. In some embodiments, the storage device 130 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memories may include a random-access memory (RAM). Exemplary RAM may include a dynamic RAM (DRAM), a double date rate synchronous dynamic RAM (DDR SDRAM), a fast page mode dynamic RAM (FPMDRAM), an extended date out dynamic RAM (EDODRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), an electrically alterable ROM (EAROM), a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected to the network 150 to communicate with one or more other components in the medical system 100 (e.g., the processing device 120, the terminal(s) 140, the imaging device 160). One or more components in the medical system 100 may access the data or instructions stored in the storage device 130 via the network 150. In some embodiments, the storage device 130 may be integrated into the medical radiation device 110.

The terminal(s) 140 may be connected to and/or communicate with the medical radiation device 110, the processing device 120, storage device 130, and/or the imaging device 160. For example, the terminal 140 may send one or more control instructions to the medical radiation device 110 to control the medical radiation device 110 to scan the subject according to the instructions. As another example, the terminal 140 may also receive the second position of the couch determined by the processing device 120, and display the second position of the couch for a user (e.g., a doctor, an operator, etc.) to confirm. In some embodiments, the terminal 140 may include a mobile device 141, a tablet computer 142, a laptop computer 143, or the like, or any combination thereof. For example, the mobile device 141 may include a mobile phone, a personal digital assistant (PDA), a gaming device, a navigation device, a point of sale (POS) device, a laptop, a tablet computer, a desktop, or the like, or any combination thereof. In some embodiments, the terminal 140 may include an input device, an output device, etc. The input device may include alphanumeric and other keys that may be input via a keyboard, a touchscreen (for example, with haptics or tactile feedback), a speech input, an eye tracking input, a brain monitoring system, or any other comparable input mechanism. Other types of the input device may include a cursor control device, such as a mouse, a trackball, or cursor direction keys, etc. The output device may include a display, a printer, or the like, or any combination thereof. In some embodiments, the terminal 140 may be a portion of the processing device 120. In some embodiments, the terminal 140 may be integrated into the processing device 120 as a console of the medical radiation device 110. For example, a use of the medical system 100 may control an operation (e.g., scanning the subject, controlling the couch 114 to move and position, etc.) of the medical radiation device 110 through the console.

The network 150 may include any suitable network that can facilitate the exchange of information and/or data for the medical system 100. In some embodiments, one or more components of the medical system 100 (e.g., the medical radiation device 110, the processing device 120, the storage device 130, the terminal(s) 140, the imaging device 160, etc.) may communicate information and/or data with one or more other components of the medical system 100 via the network 150. For example, the processing device 120 and/or the terminal 140 may obtain the data associated with the scanning range of the subject from a scanning plan from the medical radiation device 110 via the network 150. As another example, the processing device 120 and/or the terminal 140 may obtain information stored in the storage device 130 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a long term evolution (LTE) network), a frame relay network, a virtual private network (VPN), a satellite network, a telephone network, routers, hubs, witches, server computers, and/or any combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the medical system 100 may be connected to the network 150 to exchange data and/or information.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. However, those variations and modifications do not depart the scope of the present disclosure.

Figure 2:
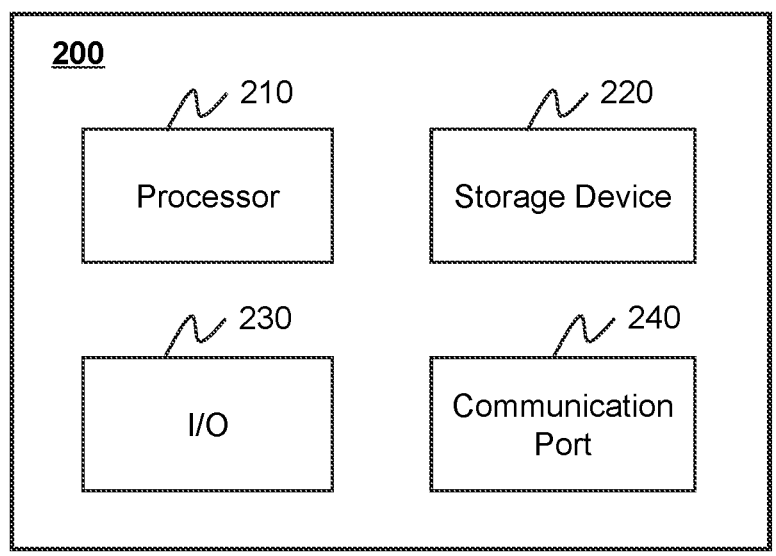
FIG. 2 is a schematic diagram illustrating exemplary hardware and/or software components of an exemplary computing device according to some embodiments of the present disclosure

FIG. 2 is a schematic diagram illustrating exemplary hardware and/or software components of an exemplary computing device according to some embodiments of the present disclosure. In some embodiments, one or more components of the medical system 100 may be implemented on one or more components of the computing device 200. Merely by way of example, the processing device 120 and/or the terminal(s) 140 may be implemented one or more components of the computing device 200, respectively.

As illustrated in FIG. 2, the computing device 200 may include a processor 210, a storage device 220, an input/output (I/O) 230, and a communication port 240. The processor 210 may execute computer instructions (e.g., program code) and perform functions of the processing device 120 in accordance with techniques described herein. The computer instructions may include, for example, routines, programs, objects, components, data structures, procedures, modules, and functions, which perform particular functions described herein. For example, the processor 210 may process image data of a subject obtained from the medical radiation device 110, the storage device 130, terminal(s) 140, the imaging device 160, and/or any other component of the medical system 100.

In some embodiments, the processor 210 may include one or more hardware processors or any circuit or processor capable of executing one or more functions, or the like, or a combination thereof. Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage device 220 may store data/information obtained from the medical radiation device 110, the storage device 130, the terminal(s) 140, the imaging device 160, and/or any other component of the medical system 100. In some embodiments, the storage device 220 may include a mass storage device, a removable storage device, a volatile read-and-write memory, a read-only memory (ROM), or the like, or any combination thereof. In some embodiments, the storage device 220 may store one or more programs and/or instructions to perform exemplary methods described in the present disclosure.

The I/O 230 may input and/or output signals, data, information, etc. In some embodiments, the I/O 230 may enable a user interaction with the computing device 200 (e.g., the processing device 120). In some embodiments, the I/O 230 may include an input device and an output device. Examples of the input device may include a keyboard, a mouse, a touch screen, a microphone, or the like, or any combination thereof. Examples of the output device may include a display device, a loudspeaker, a printer, a projector, or the like, or any combination thereof. Examples of the display device may include a liquid crystal display (LCD), a light-emitting diode (LED)-based display, a flat panel display, a curved screen, a television device, a cathode ray tube (CRT), a touch screen, or the like, or any combination thereof.

The communication port 240 may be connected to a network (e.g., the network 150) to facilitate data communications. The communication port 240 may establish connections between the computing device 200 (e.g., the processing device 120) and one or more components of the medical system 100 (e.g., the medical radiation device 110, the storage device 130, the terminal(s) 140, and/or the imaging device 160). The connection may be a wired connection, a wireless connection, any other communication connection that can enable data transmission and/or reception, and/or a combination of these connections. The wired connection may include, for example, an electrical cable, an optical cable, a telephone wire, or the like, or a combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or any combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
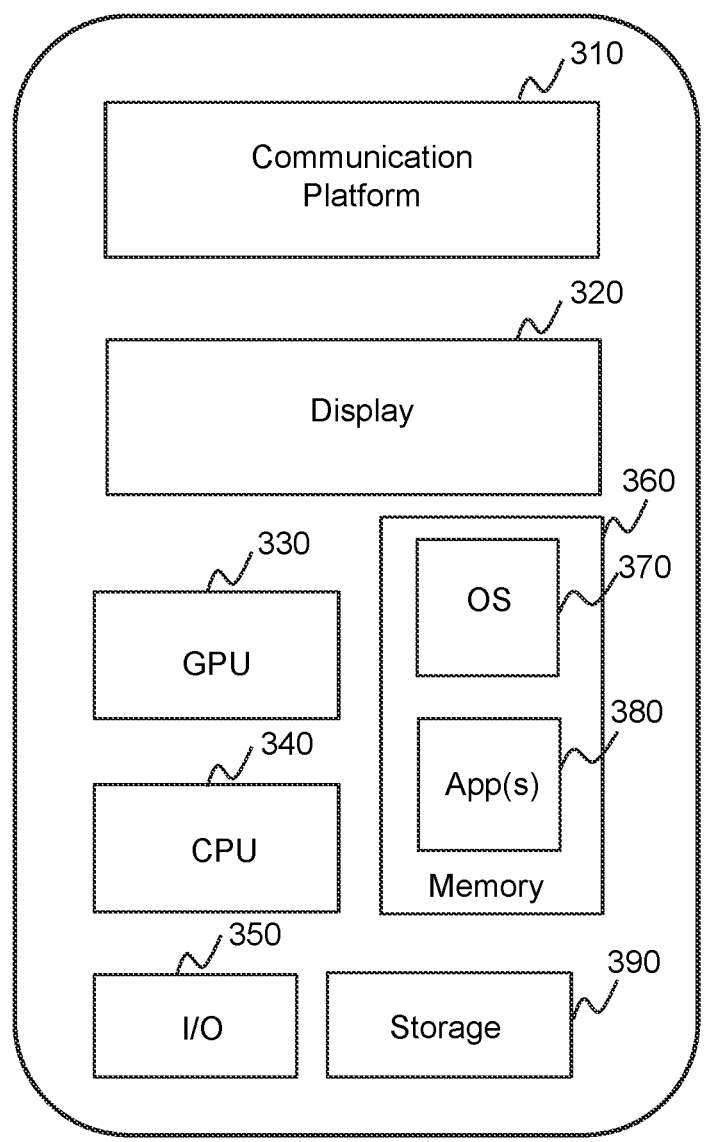
FIG. 3 is a schematic diagram illustrating exemplary hardware and/or software components of an exemplary mobile device on which a terminal device may be implemented according to some embodiments of the present disclosure.

FIG. 3 is a schematic diagram illustrating exemplary hardware and/or software components of an exemplary mobile device on which a terminal device may be implemented according to some embodiments of the present disclosure. In some embodiments, one or more components of the medical system 100 may be implemented on one or more components of the mobile device 300. Merely by way of example, the terminal 140 may be implemented on one or more components of the mobile device 300.

As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™, etc.) and one or more applications 380 may be loaded into the memory 360 from the storage 390 in order to be executed by the CPU 340. The applications 380 may include a browser or any other suitable mobile apps for receiving and rendering information relating to the medical system 100. User interactions with the information stream may be achieved via the I/O 350 and provided to the processing device 120 and/or other components of the medical system 100 via the network 150.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal. A computer may also act as a server if appropriately programmed.

Figure 4:
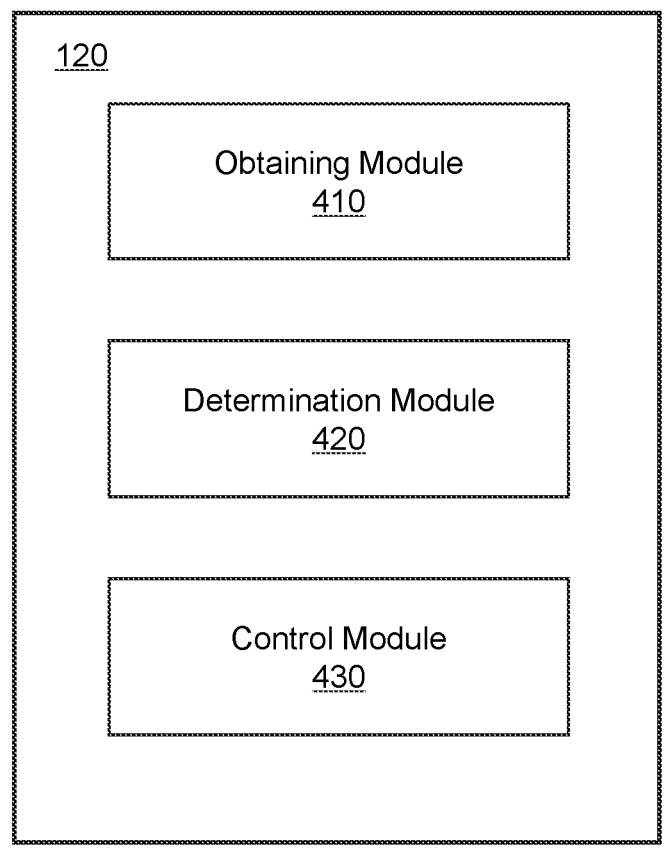
FIG. 4 is a schematic diagram illustrating an exemplary processing device according to some embodiments of the present disclosure.

FIG. 4 is a schematic diagram illustrating an exemplary processing device according to some embodiments of the present disclosure. In some embodiments, the processing device 120 may include an obtaining module 410, a determination module 420, and a control module 430. In some embodiments, the modules may be hardware circuits of all or part of the processing device 120. The modules may also be implemented as an application or set of instructions read and executed by the processing device 120. Further, the modules may be any combination of the hardware circuits and the application/instructions. For example, the modules may be part of the processing device 120 when the processing device 120 is executing the application/set of instructions.

The obtaining module 410 may be configured to obtain data and/or information associated with the medical system 100. The data and/or information associated with the medical system 100 may include data associated with a scanning range of a subject, an image of the subject on a couch of the medical radiation device, etc. More descriptions for obtaining data associated with the scanning range of the subject may be found elsewhere in the present disclosure (e.g., operation 510 as described in FIG. 5).

The determination module 420 may be configured to determine data and/or information associated with the medical system 100. In some embodiments, the determination module 420 may determine the position of the scanning range of the subject in the image. In some embodiments, the determination module 420 may determine a moving distance from a first position to a second position based on the position of the scanning range of the subject in the image when the couch is at the first position. For example, the determination module 420 may determine, based on the position of the scanning range in the image, a first distance between a starting position of the scanning range and a radiation region when the couch is at the first position. As another example, the processing device 120 may determine, based on the position of the scanning range in the image, a second distance between an ending position of the scanning range and the radiation region when the couch is at the first position. The processing device 120 may determine, based on the first distance and/or the second distance, the moving distance of the couch from the first position to the second position. In some embodiments, the determination module 420 may determine the second position based on the position of the scanning range of the subject in the image when the couch is at the first position. For example, the determination module 420 may determine the second position based on the first distance and/or the second distance. More descriptions regarding the determination of data and/or information associated with the medical system 100 may be found elsewhere in the present disclosure (e.g., FIGS. 5, 7-8, and descriptions thereof).

The control module 430 may be configured to control a component (e.g., the medical radiation device 110) of the medical system 100. For example, the control module 430 may cause a couch of a medical radiation device to move to the second position based on the moving distance or the second position determined by the determination module 420.

It should be noted that the above description of the processing device 120 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more modules may be combined into a single module. For example, the obtaining module 410 and the determination module 420 may be combined into a single module. In some embodiments, one or more modules may be added or omitted in the processing device 120. For example, the control module 430 may be omitted. As another example, a storage module (not shown in FIG. 4) may be added to the processing device 120. The storage module may be configured to store information (e.g., data associated with a scanning range of a subject, an image of the subject on a couch of a medical radiation device, a first position, a position of the scanning range of the subject in the image, a second position, a radiation region of the medical radiation device, etc.) associated with the medical system 100.

Figure 5:
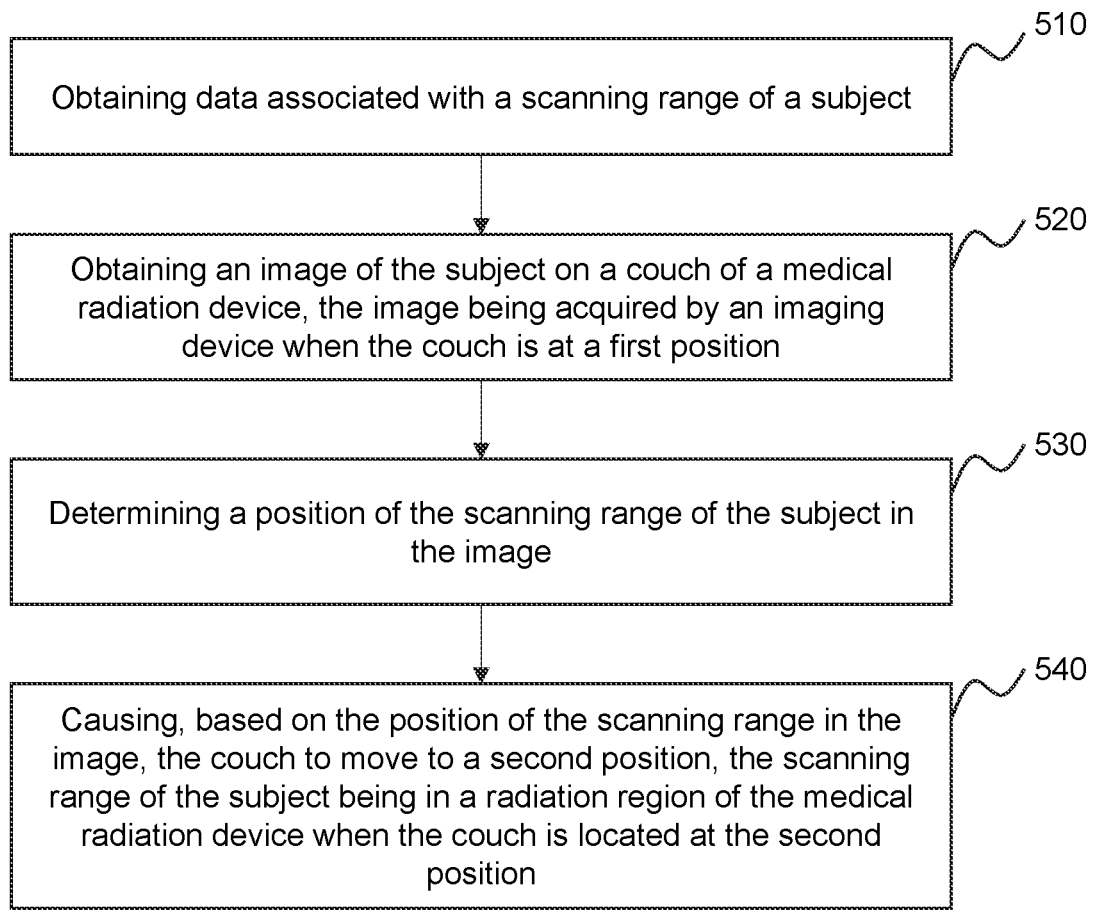
FIG. 5 is a flowchart illustrating an exemplary process for positioning a subject in a medical procedure according to some embodiments of the present disclosure.

FIG. 5 is a flowchart illustrating an exemplary process for positioning a subject in a medical procedure according to some embodiments of the present disclosure. As used herein, the positioning a subject refers to moving the subject to a desired position in the radiation region, for example, with a desired posture. In some embodiments, process 500 may be implemented in the medical system 100 or the medical system 200 illustrated in FIG. 1. For example, the process 500 may be stored in the storage device 130 and/or the storage (e.g., the storage device 220, the storage 390) as a form of instructions, and invoked and/or executed by the processing device 120 (e.g., the processor 210 of the computing device 200 as illustrated in FIG. 2, the CPU 340 of the mobile device 300 as illustrated in FIG. 3). The operations of the illustrated process presented below are intended to be illustrative. In some embodiments, the process 500 may be accomplished with one or more additional operations not described, and/or without one or more of the operations discussed. Additionally, the order in which the operations of the process 500 as illustrated in FIG. 5 and described below is not intended to be limiting.

In 510, the processing device 120 (e.g., the obtaining module 410) may obtain data associated with a scanning range of a subject.

In some embodiments, the subject may include a patient, a man-made object, etc. In some embodiments, the subject may include a specific portion, organ, and/or tissue of a patient. For example, the subject may include the head, the brain, the neck, a body, the shoulder, an arm, the thorax, the heart, the stomach, a blood vessel, a soft tissue, a knee, a foot, or the like, or any combination thereof.

The scanning range of the subject may refer to a range or a portion of the subject that needs to receive a scan (e.g., imaging or treatment) using a medical radiation device. For example, the scanning range of the subject may be a portion of the subject including an anomaly that is determined in a previous diagnosis or scan. As another example, the scanning range of the subject may include a range of a designated organ and/or tissue.

Figure 6:
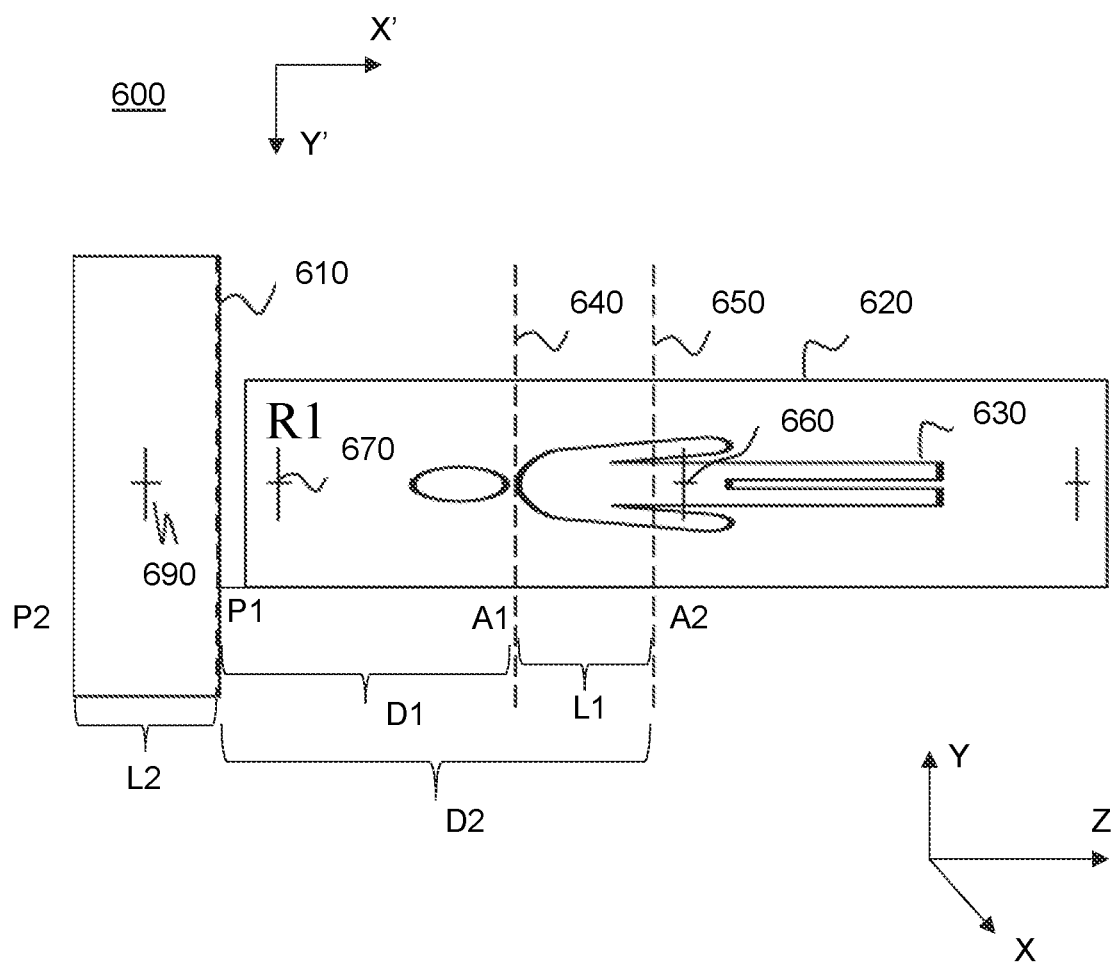
FIG. 6 is a schematic diagram illustrating a partial structure of a medical system according to some embodiments of the present disclosure.

In some embodiments, the data associated with the scanning range of the subject may include data associated with the subject, data for identifying the scanning range, etc. The data associated with the subject may include a name, height, weight, gender, age, an identity card number, a social security number, a medical history, etc., of the subject. The data for identifying the scanning range may include a name, a position (e.g., a starting position, a center position, an ending position), etc., of the scanning range in the subject, etc. The starting position of the scanning range refers to a location on the subject where the scan of the subject starts. The ending position of the scanning range refers to a location on the subject where the scan of the subject ends. In some embodiments, the starting position may indicate a position of a cross-section of the subject perpendicular to a direction (e.g., the long axis of the subject or the couch); the ending position may indicate a position of another cross-section of the subject perpendicular to the direction (e.g., the long axis of the subject or the couch). For example, referring to FIG. 6, FIG. 6 is a schematic diagram illustrating a partial structure of a medical system according to some embodiments of the present disclosure. FIG. 6 shows a vertical view of the couch and the medical radiation device. A subject 630 may be lying on a couch 620. The scanning range of the subject 630 may include a region from a starting position 640 to an ending position 650 along a Z-axis of the medical radiation device. The starting position 640 may indicate a Z-axis position of a cross-section of the subject that is perpendicular to the Z-axis, that is denoted by a line 640; the ending position may indicate a Z-axis position of another cross-section of the subject perpendicular to the Z-axis, that is denoted by a line 650. After moving the couch 620 into the scanning region in a gantry 610, the subject may be scanned from the starting position 640. The scan may be stopped when the ending position 650 is scanned. The center position of the scanning range may be a position of a geometric center of a portion of the subject within the scanning range, e.g., a Z-axis position of the geometric center, a Y-axis position of the geometric center, or a Y-axis position of the geometric center, or the combination thereof.

In some embodiments, the starting position and the ending position may correspond to a first anatomical location of the subject and a second anatomical location of the subject, respectively. An anatomical location of the subject (e.g., a human body) refers to a position corresponding to an anatomical structure of the subject. In some embodiments, the anatomical location of the subject may be configured to identify the starting position and/or the ending position of the scanning range. For example, the names of the first anatomical location and the second anatomical location of the subject may be used to identify the starting position and/or the ending position of the scanning range, respectively. The starting positon and the ending position may be denoted by a staring line and an ending line perpendicular to the long axis of the subject that is parallel to the Z-axis of the medical radiation device. For example, as shown in FIG. 6, the first anatomical location corresponding to the starting position 640 may be the C5 cervical spine of the subject 630. The second anatomical location corresponding to the ending position 650 may be the T11 lumbar spine of the subject 630. That is, the scanning range may be from the C5 cervical spine to the T11 lumbar spine. The starting position 640 and the ending position 650 may be denoted as two lines that are perpendicular to the long axis of the subject that is parallel to the Z-axis of the medical radiation device. By corresponding the starting position and the ending position to the first anatomical location and the second anatomical location, respectively, the scanning range may be determined or identified by an internal structure of the subject, thereby improving the accuracy of the scanning range. In some embodiments, joints in the anatomical structure may be further used to determine or identify the starting position and the ending position. Exemplary joints may include a hip joint, a knee joint, a shoulder joint, or the like, or any combination thereof.

In some embodiments, the processing device 120 may obtain the data associated with the scanning range of the subject from a scanning plan. For example, the processing device 120 may obtain the starting position and the ending position from the scanning plan. In some embodiments, the scanning plan may include plan parameters in a scanning protocol. The plan parameters may include a type of a medical radiation device (e.g., the medical radiation device 110), a planned scanning range of the subject (e.g., the starting position and the ending position of the scan), a scanning duration of the subject, a scheduled scanning time, information of the scanning range, information of the subject, scanning parameters (e.g., tube current, tube voltage, slice information), etc. For example, when a subject is registered for scanning, a CT device may be determined to scan the head of the subject according to a historical medical record of the subject (e.g., a medical history and a scanning history displayed in an electronic medical record of the subject). Accordingly, a head scanning plan for the subject may be determined. In some embodiments, the scanning plan may be stored in a medical radiation device (e.g., the medical radiation device 110), a terminal (e.g., the terminal 140), a storage device (e.g., the storage device 130, the storage device 220, the storage 390), a database, etc. Therefore, the processing device 120 may obtain the scanning range from the medical radiation device, the terminal, the storage device, the database, etc.

In some embodiments, the processing device 120 may obtain the data associated with the scanning range of the subject according to an input of a user (e.g., a doctor, an operator, a technician, etc.). For example, the processing device 120 may obtain the starting position and the ending position input by a user, and designate the starting position and the ending position input by the user as the starting position and the ending position of the scanning range. In some embodiments, the user may input the starting position and the ending position (e.g., from the C5 cervical spine to the T11 lumbar spine) from the terminal 130 by manual input, a voice input, etc.

In some embodiments, the processing device 120 may adjust the data associated with the scanning range of the subject based on an instruction of the user. For example, the user may adjust the starting position and the ending position in a scanning protocol (or the scanning plan) to configure (e.g., create, adjust, etc.) the scanning range in the scanning protocol (or the scanning plan), and determine the starting position and the ending position of the scanning range based on the configuration result.

In some embodiments, the processing device 120 may determine the scanning range based on an interaction between the user and the processing device 120 through a user interface. In some embodiments, the user interface may be used for configuring a scanning protocol (or a portion of the scanning plan). In some embodiments, the user interface may include multiple operating controls. Each of the multiple operating controls may correspond to one of the multiple anatomical locations. The processing device 120 may cause a display device to present the user interface including multiple operating controls (e.g., buttons). In some embodiments, the user interface may include a human anatomical structure map that includes multiple anatomical locations. More descriptions regarding the user interface may be found elsewhere in the present disclosure (e.g., FIG. 9 and descriptions thereof). In some embodiments, the user may visually operate the multiple operating controls to configure the starting position and the ending position of the scanning range in the scanning protocol.

Further, the processing device 120 may determine the data associated with the scanning range of the subject in response to receiving an input of the user through the multiple operating controls. For example, the processing device 120 may receive an operation of the user on one or more of the multiple operating controls. The processing device 120 may determine, based on the operation of the user on the one or more of the multiple operating controls, a configuration of the scanning range in the scanning protocol. The processing device 120 may further determine, based on the configuration of the scanning range, the data associated with the scanning range of the subject. For example, the user may use a button to select an anatomical location corresponding to the button to determine the starting position or the ending position.

In some embodiments, the user interface may present an image of the subject. The user may select or drag a preset point (e.g., a cursor) on the image of the subject displayed by the terminal 130 to input the starting position and the ending position.

In 520, the processing device 120 (e.g., the obtaining module 410) may obtain an image of the subject on a couch of the medical radiation device.

The medical radiation device may be configured to scan (e.g., imaging or treat) the subject (e.g., imaging or treat). For example, the medical radiation device may include a positron emission tomography (PET) device, a single-photon emission computed tomography (SPECT) device, a computed tomography (CT) device, a magnetic resonance imaging (MRI) device, a radiation therapy (RT) device, or the like, or any combination thereof. The couch may be a portion of the medical radiation device. In some embodiments, the couch may be configured to support the subject. More descriptions regarding the medical radiation device may be found elsewhere in the present disclosure (e.g., FIG. 1 and descriptions thereof).

In some embodiments, the image (also referred to as a positioning image) may be acquired by an imaging device when the couch is at a first position. The first position refers to the position of the couch in space before the scanning. In some embodiments, the first position of the couch may also be referred to as a current position of the couch. For example, the first position may include an initial position when the subject is lying on the couch, a position before the couch is entered the gantry, or any other position before the couch arrives at the desired position (e.g., the second position), etc. As used herein, the desired position of the couch refers to a position of the couch that the scanning range of the subject is located in the radiation region of the medical radiation device (e.g., a center of the scanning range may coincide with the isocenter of the medical radiation device), or a position range from a position that the starting position of the scanning range enters the radiation region to a position that the ending position of the scanning range enters the radiation region or a position range from a position that the ending position of the scanning range enters the radiation region to a position that the starting position of the scanning range leaves the radiation region.

In some embodiments, the first position may be represented by position information of the couch, such as coordinates of a reference point (e.g., a central point, a front point, a rear point, etc.) of the couch in a spatial coordinate system (also referred to as a second coordinate system). For example, the first position may be denoted as a first couch code (also referred to as a current couch code).

In some embodiments, the image may represent the contour (e.g., a 3D contour) of the subject and/or at least a portion of the couch. The image may include a static image, a video, an image sequence including multiple static images, etc. In some embodiments, the image may include the couch and the subject. For example, the image of the subject may be an image that a subject is located on a couch when the couch is located at the first position. In some embodiments, the image may be configured to position the scanning range of the subject before the scanning. That is, the image may be configured to position the anatomical locations (e.g., the first anatomical location and the second anatomical location) of the subject corresponding to the scanning range of the subject that needs to receive a scan (e.g., imaging or treatment) using the medical radiation device.

The imaging device may include one or more visual sensors, one or more thermal imaging sensors, one or more radars, etc. For example, the imaging device may include a three-dimensional (3D) camera, which may acquire a 3D image of the subject. As another example, the imaging device may include a depth camera. Depth information of the subject may be obtained. The depth information of the subject may indicate distances between points on the contour profile of the subject and a reference position (e.g., an optical center of the imaging device). More descriptions regarding the imaging device may be found elsewhere in the present disclosure (e.g., FIG. 1 and descriptions thereof). In some embodiments, the imaging device may be disposed of above the couch. Therefore, the image may be acquired from an overlooking view of the subject by the imaging device that is located above the couch. In some embodiments, the imaging device may be above a side of the couch. In some embodiments, the imaging device may be fixed above the couch. That is, a position of the imaging device may be fixed to the medical radiation device (e.g., a portion of the medical radiation device 110). Therefore, the position of the imaging device may be static during the scanning, which may simplify the positioning, reduce the amount of calculation, and improve the accuracy of the positioning.

In some embodiments, the processing device 120 may directly obtain the image of the subject on the couch of the medical radiation device from the imaging device 160. For example, the imaging device may transmit the acquired image to the processing device 120 via the network 150. In some embodiments, the imaging device may transmit the image of the subject on the couch of the medical radiation device to a medical radiation device (e.g., the medical radiation device 110), a terminal (e.g., the terminal 140), a storage device (e.g., the storage device 130, the storage device 220, the storage 390), a database, etc. Further, the processing device 120 may access the medical radiation device, the terminal, the storage device, the database, etc., and retrieve the image of the subject on the couch.

In 530, the processing device 120 (e.g., the determination module 420) may determine a position of the scanning range of the subject in the image.

The position of the scanning range of the subject in the image may include at least one of the starting position corresponding to the first anatomical location of the subject and the ending position corresponding to the second anatomical location of the subject. The starting position corresponding to the first anatomical location of the subject in the image may be denoted by coordinates of the starting position in a first coordinate system applied to the image, a position relationship between the starting position and a reference position (e.g., a point on the couch, a point on the medical radiation device). For example, the starting position in the image may be denoted by a distance between the starting position to a front end of the couch that is close to the radiation region of the medical radiation device along the Z-axis of the medical radiation device; the ending position in the image may be denoted by a distance between the ending position to the front end of the couch along the Z-axis of the medical radiation device. As another example, the starting position in the image may be denoted by a distance between the starting position to a front end of the radiation region that is close to the couch along the Z-axis of the medical radiation device, the ending position in the image may be denoted by a distance between the ending position to the front end of the radiation region along the Z-axis of the medical radiation device. As still another example, the processing device 120 may denote the starting position corresponding to the first anatomical location of the subject and the ending position corresponding to the second anatomical location of the subject using a first coordinate system applied to the image. For example, the processing device 120 may determine coordinates of the starting position and the ending position in the first coordinate system and use the coordinates of the starting position and the ending position in the first coordinate system to denote scanning range. The starting position in the image may be denoted by the same coordinate (e.g., Y' coordinate in the first coordinate system as shown in FIG. 6) of points on the starting line corresponding to the starting position; the ending position in the image may be denoted by the same coordinate (e.g., Y' coordinate in the first coordinate system as shown in FIG. 6) of points on the ending line corresponding to the ending position.

In some embodiments, the processing device 120 may determine, based on the data associated with the scanning range, the position of the scanning range of the subject in the image using a trained machine learning model. For example, the trained machine learning model may include an anatomical location recognition model. In some embodiments, the anatomical location recognition model may be configured to identify or recognize locations of multiple types of anatomical structures of a subject from the image. In some embodiments, the anatomical location recognition model may be a model configured to identify or recognize a location of a particular type of anatomical structure (e.g., the soft tissue, the bone, the joint, etc.) or identify or recognize locations of multiple types of anatomical structures of a particular type of people (e.g., children, the old, women, men, etc). The processing device 120 may determine, based on the data associated with the scanning range, the anatomical location recognition model from multiple models corresponding to multiple types of anatomical structures or multiple types of people. The processing device 120 may process the image of the subject using the anatomical location recognition model to determine the position of the scanning range of the subject in the image. For instance, the processing device 120 may input the image of the subject to the anatomical location recognition model, and the anatomical location recognition model may output the image marked with the anatomical location. The processing device 120 may determine the position of the scanning range of the subject in the image based on the image marked with the multiple anatomical locations. For example, the processing device 120 may compare the multiple anatomical locations marked in the image with the first anatomical location corresponding to the starting position and the second anatomical location corresponding to the ending position of the scanning range to determine the starting position and the ending position of the scanning range.

In some embodiments, the processing device 120 may process, based on the data associated with the scanning range, the image of the subject using the anatomical location recognition model to determine the position of the scanning range of the subject in the image. For instance, the processing device 120 may input the image of the subject and the data associated with the scanning range to the anatomical location recognition model, and the anatomical location recognition model may output the image marked with the scanning range.

In some embodiments, the anatomical location recognition model may include a neural network model, a logistic regression model, a support vector machine, etc. Merely by way of example, the anatomical location recognition model may be a neural network model. The neural network model may include multiple layers, such as an input layer, one or more convolutional layers, one or more nonlinear activation layers, one or more pooling layers, one or more fully connected layers, and/or an output layer. The input layer of the neural network model may obtain images of the subject on the couch (and/or the data associated with the scanning range acquired in 510). The intermediate layers (e.g., the one or more convolutional layers, the one or more nonlinear activation layers, the one or more pooling layers, the one or more fully connected layers, etc.) may extract and/or distinguish visual features or styles from the images. The output layer may output the images with identified features or styles (e.g., the anatomical location). For example, a feature identifier or a feature vector may be used to mark the recognized anatomical location. In some embodiments, the recognized anatomical location may include a representative joint, such as a cervical vertebra C5, a shoulder joint, an elbow joint, a wrist joint, a lumbar vertebra T11, a hip joint, a knee joint, an ankle joint, etc.

In some embodiments, an initial anatomical location recognition model may be trained based on a plurality of training samples with labels. Each of the plurality of training samples may be an image of a sample subject, and the corresponding label may include one or more representative anatomical locations marked in the image of the sample subject. In some embodiments, the labels of the training samples may be added by manual labeling or other manners.

In some embodiments, the plurality of training samples with labels may be input to the initial anatomical location recognition model. Model parameters of the initial anatomical location recognition model may be updated iteratively until the training is completed. In some embodiments, a training algorithm (e.g., a back propagation algorithm) may be used to train the initial anatomical location recognition model and update the model parameters. For example, a predicted result of each anatomical location identified by the initial anatomical location recognition model may be compared to an actual result of the anatomical location (i.e., the label) of the training sample to obtain a comparison result. The comparison result may be used to represent an error between the predicted result and the actual result corresponding to each anatomical location. A loss function may be constructed based on a sum of the comparison results of the anatomical locations in the training sample. In some embodiments, each of the comparison results may be designated a weighting coefficient. The weighting coefficient may be determined based on parameters (e.g., a position, a structure, etc.) of the anatomical location. The loss function may be constructed based on a weighting sum of the comparison results. The model parameters may be adjusted to make the loss function as small as possible (or convergence) until the training is completed.

In some embodiments, the processing device 120 may determine the position of the scanning range of the subject in the image using another manner, such as a template matching algorithm. For example, reference templates and software that can operate the template matching algorithm may be stored in the processing device 120. Each of the reference templates may include a reference image corresponding to a reference scanning range and the reference scanning range may be marked in the reference image. The processing device 120 may determine one or more candidate templates based on the data associated with the scanning range. For example, the reference scanning ranges corresponding to the one or more candidate templates may be the same as the scanning range determined in 520. The processing device 120 may determine a target template that matches with the image from the one or more candidate templates and designate the position of the reference scanning range marked in the target template that matches with the image as the position of the scanning range in the image. In some embodiments, the processing device 120 may determine the target template from the one or more candidate templates by determining a similarity between the image and each of the one or more candidate templates based on image features. A candidate template that has a maximum similarity between the image may be considered to match the image and may be designated as the target template. The image features may include, such as a shape, a texture, a color, a grayscale, etc. After obtaining the image of the subject and the data for identifying the scanning range of the subject, the processing device 120 may determine the one or more candidate templates corresponding to the scanning range based on the data associated with the subject. Accordingly, the processing device 120 may operate the software of the template matching algorithm (e.g., a similarity matching algorithm) to process the image based on the one or more candidate templates corresponding to the scanning range. The processing device 120 may determine the position of the scanning range of the subject in the image by matching the one or more candidate templates with the image based on the image features such as the shape, the texture, the color, the grayscale, etc., of the image.

In 540, the processing device 120 (e.g., the determination module 420) may cause, based on the position of the scanning range in the image, the couch to move to a second position. The scanning range of the subject may be in a radiation region of the medical radiation device when the couch is located at the second position.

The second position of the couch refers to a position where the couch is located during the scanning of the subject. That is, when the couch is located at the second position, the scanning range of the subject may be in the radiation region of the medical radiation device. In some embodiments, the length of the scanning range of the subject along the Z-axis may be greater than the length of the radiation region of the medical radiation device, so that the couch may be moved during the scanning to cause the ending position of the scanning range enters the radiation region. Therefore, the second position may include a position range, such as a position range from a position that the starting position of the scanning range enters the radiation region to a position that the ending position of the scanning range enters the radiation region. In some embodiments, the length of the scanning range of the subject along the Z-axis may be less than the length of the radiation region of the medical radiation device, so that the couch may be moved to the second position to cause the scanning range is located in the radiation region. The second position may include a position in a position range from a position that the ending position of the scanning range enters the radiation region to a position that the starting position of the scanning range leaves the radiation region. For example, the second position may be such that the center of the scanning range coincides with the center of the radiation region or isocenter of the medical radiation device. As another example, the second position may be such that the ending position of the scanning range enters the radiation region.

In some embodiments, the processing device 120 may determine a moving distance from the first position to the second position based on the position of the scanning range in the image. The processing device 120 may cause the couch to move to the second position based on the moving distance. In some embodiments, the processing device 120 may determine the second position based on the position of the scanning range in the image and the first position. For example, the processing device 120 may determine the second position based on the moving distance and the first position. The processing device 120 may cause the couch to move to the second position based on the second position.

In some embodiments, the processing device 120 may determine, based on the position of the scanning range in the image, a first distance between the starting position of the scanning range and the radiation region when the couch is at the first position. The processing device 120 may determine, based on the position of the scanning range in the image, a second distance between the ending position of the scanning range and the radiation region when the couch is at the first position. More descriptions regarding the determination of the first distance and the second distance may be found elsewhere in the present disclosure (e.g., FIG. 7 and descriptions thereof). The processing device 120 may determine the moving distance based on at least one of the first distance or the second distance. As used herein, a distance between the position (e.g., the starting position and the ending position) of the scanning range and the radiation region when the couch is at the first position refers to a spatial distance between the position (e.g., the starting position and the ending position) of the scanning range and a reference position of the radiation region along the Z-axis of the radiation region. In some embodiments, the reference position of the radiation region may be a position that is closest to the couch (e.g., the edge) or a center position of the radiation region.

In some embodiments, the processing device 120 may determine whether a length (i.e., L1 in FIG. 6) of the scanning range of the subject is larger than the length of the radiation region (i.e., L2 in FIG. 6). If the length (i.e., L1 in FIG. 6) of the scanning range of the subject is less than or equal to the length of the radiation region (i.e., L2 in FIG. 6), the second position may include a position in a position range from a position that the ending position of the scanning range enters the radiation region to a position that the starting position of the scanning range leaves the radiation region. The moving distance of the couch may be in a distance range from a minimum moving distance that the ending position of the scanning range enters the radiation region to a maximum moving distance that the starting position of the scanning range leaves the radiation region. The maximum moving distance and the minimum moving distance may be determined based on the first distance and/or the second distance. For example, FIG. 6 is a schematic diagram illustrating a determination of the moving distance according to some embodiments of the present disclosure. If the reference position of the radiation region is located closest to the couch as shown in FIG. 6, i.e., an edge of the radiation region close to the couch indicated by the dashed line 610, the minimum moving distance (denoted as Dmin) may be equal to the second distance (denoted as D2) or equal to a sum between the first distance (denoted as D1) and the length (i.e., L1) of the scanning range along the Z-axis (i.e., D=D1+L1), such that when the couch moves the minimum moving distance, the ending position enters the radiation region and arrives at the reference position 610 and the scanning range may be within the radiation region; the maximum moving distance (denoted as Dmax) may be equal to a sum of the first distance (denoted as D1) and the length (i.e., L2) of the radiation region along the Z-axis (i.e., D=D1+L2), such that when the couch moves a distance less than the maximum moving distance, the starting position is still within the radiation region.

In some embodiments, no matter whether the length (i.e., L1 in FIG. 6) of the scanning range of the subject is larger than or less than a length of the radiation region (i.e., L2 in FIG. 6), the second position may include a position range from a position that the starting position of the scanning range enters the radiation region to a position that the ending position of the scanning range enters the radiation region. The moving distance of the couch may be in a distance range from a minimum moving distance that the starting position of the scanning range enters the radiation region to a maximum moving distance that the ending position of the scanning range enters the radiation region. The maximum moving distance and the minimum moving distance may be determined based on the first distance and/or the second distance. For example, as shown in FIG. 6, if the reference position of the radiation region is located closest to the couch as shown in FIG. 6, i.e., an edge of the radiation region close to the couch indicated by the dashed line 610, the minimum moving distance (denoted as Dmin) may be equal to the second distance (denoted as D1) or equal to a difference between the second distance (denoted as D2) and the length (i.e., L1) of the scanning range along the Z-axis (i.e., Dmin=D2−L1), such that when the couch moves the minimum moving distance, the starting position enters the radiation region and arrives at the reference position 610; the maximum moving distance (denoted as Dmax) may be equal to the second distance (denoted as D2), such that when the couch moves the maximum moving distance, the ending position enters the radiation region.

In some embodiments, the processing device 120 may determine, based on the moving distance and the first position, a position range of the couch. The position range (also referred to a target couch code) of the couch may refer to a coordinate range of the couch in the second coordinate system when the first anatomical location and the second anatomical location of the subject are transferred to the radiation region of the medical radiation device. The radiation region of the medical radiation device may refer to a range covered by the radiation beams emitted by a radioactive source of the medical radiation device, or a region corresponding to a detector of the medical radiation device along the X-axis. More descriptions regarding the determination of the position range of the couch may be found elsewhere in the present disclosure (e.g., FIG. 8 and descriptions thereof).

In some embodiments, the processing device 120 may cause the couch to move to the second position from the first position. For example, the processing device 120 may determine a moving distance of the couch between the second position and the first position. The moving distance of the couch may include a first moving distance along the horizontal direction (e.g., the Z-axis direction) and a second moving distance along the vertical direction (e.g., the Y-axis direction). The first moving distance may be configured to adjust a distance between the couch and the radiation region. The second moving distance may be configured to adjust a distance between the couch and a center of the radiation region. Accordingly, the processing device 120 may cause the couch to move based on the moving distance of the couch (e.g., the first moving distance and the second moving distance).

In some embodiments, before moving the couch, the processing device 120 may output, through the user interface, the second position to a terminal (e.g., the terminal 140) of the user. The user may determine and/or adjust the second position displayed on the user interface. After receiving a determination and/or an adjustment instruction for adjusting the second position provided by the user through the user interface, the processing device 120 may cause, based on the determination and/or the adjustment instruction, the couch to move. For example, if the first position is Q1, the second position is Q2, and the adjusted second position is Q3, the processing device 120 may move the couch based on the first position Q1 and the adjusted second position Q3.

In some embodiments of the present disclosure, the data associated with the scanning range of the subject may be obtained. The data associated with the scanning range of the subject may include a starting position corresponding to a first anatomical location of the subject and an ending position corresponding to a second anatomical location of the subject. The position of the scanning range of the subject in the image may be accurately determined. Accordingly, the second position may be determined automatically, which may need no observation on the subject by the user. Therefore, the dependence on the experience of the user may be reduced, thereby improving the efficiency of positioning the couch.

In some embodiments, the processing device 120 may need not determine the second position based on the first distance and/or the second distance. The processing device 120 may cause the couch to move a distance, such that the couch may arrive at the second position.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more other optional operations may be added in process 500. For example, an operation for storing information (e.g., the data associated with the scanning range of the subject, the image of the subject on the couch of the medical radiation device, the position of the scanning range of the subject in the image, the first position, the second position, etc.) associated with the medical system 100 may be added in process 500.

FIG. 7 is a flowchart illustrating an exemplary process for determining a second position of a couch according to some embodiments of the present disclosure. In some embodiments, process 700 may be implemented in the medical system 100 or the medical system 200 illustrated in FIG. 1. For example, the process 700 may be stored in the storage device 130 and/or the storage (e.g., the storage device 220, the storage 390) as a form of instructions, and invoked and/or executed by the processing device 120 (the processor 210 of the computing device 200 as illustrated in FIG. 2, the CPU 340 of the mobile device 300 as illustrated in FIG. 3). The operations of the illustrated process presented below are intended to be illustrative. In some embodiments, the process 700 may be accomplished with one or more additional operations not described, and/or without one or more of the operations discussed. Additionally, the order in which the operations of the process 700 as illustrated in FIG. 7 and described below is not intended to be limiting. In some embodiments, the operation 540 may be achieved according to the process 700.

In 710, the processing device 120 (e.g., the obtaining module 410) may obtain a transforming relationship between a first coordinate system applied to an image and a second coordinate system.

In some embodiments, the image may be acquired by an imaging device (e.g., the imaging device 160) when the couch is at a first position. The first position refers to a position of the couch in space before the scanning. In some embodiments, the first position of the couch may also be referred to as a current position of the couch. More descriptions for the image and the subject may be found elsewhere in the present disclosure (e.g., FIG. 5 and the descriptions thereof).

The first coordinate system may be used to denote a position of different parts of the subject in the image. For example, the different parts of the subject may be represented by pixels or voxels in the image. The position of different parts of the subject in the image may be denoted as positions of corresponding pixels or voxels in the image using the first coordinate system. In some embodiments, the image may be two-dimensional, and the first coordinate system may be two dimensions. Merely by way of example, a vertex of the image may be determined as an origin of the first coordinate system. One side of the image may be determined as an X'-axis of the first coordinate system. Another side that is perpendicular to the X'-axis may be determined as a Y'-axis of the first coordinate system. It should be noted that the first coordinate system is merely provided as an exemplary first coordinate system, and not intended to limit the scope of the present disclosure. For example, a center point of the image may be determined as the origin of the first coordinate system. The following descriptions are provided regarding the first coordinate system including the Y'-axis along the long axis of the couch, and the X'-axis along a short axis of the couch' unless otherwise stated. It should be noted that the descriptions of the first coordinate system including the Y'-axis along the long axis of the couch, and the X'-axis along a short axis of the couch in the present disclosure are merely provided for illustration, and not intended to limit the scope of the present disclosure.

In some embodiments, a second coordinate system (also referred to as the spatial coordinate system) may be established based on the position of a medical radiation device (e.g., the medical radiation device 110). Merely by way of example, a scanning center point (e.g., isocenter) of the medical radiation device may be determined as an origin of the second coordinate system. A long axis of the medical radiation device may be determined as a Z-axis of the second coordinate system. A plane defined by an X-axis and a Y-axis of the second coordinate system may be perpendicular to the Z-axis. In some embodiments, a short axis of the medical radiation device may be determined as the X-axis. A direction perpendicular to a plane defined by the X-axis and the Z-axis may be determined as a Y-axis. In some embodiments, the couch may be caused to move along the X-axis, the Y-axis, and/or the Z-axis of the second coordinate system. For example, the couch may be moved in and out of the radiation region along the Z-axis, and adjusted along the Y-axis and/or the X-axis. It should be noted that the second coordinate system is merely provided as an exemplary second coordinate system, and not intended to limit the scope of the present disclosure. For example, a radioactive source may be determined as the origin of the second coordinate system.

The transforming relationship between the first coordinate system and the second coordinate system may be used to perform a transform between characteristic information of a subject represented in the image (i.e., denoted by the first coordinate system) to characteristic information of the subject in the space (i.e., denoted by the second coordinate system) refers to a corresponding relationship between a position in the image and coordinates of the position in the second coordinate system. The characteristic information may include a position, a size (e.g., an area, a length, a width, a thickness, etc.). For example, the transforming relationship between the first coordinate system applied to the image and the second coordinate system may be used to transform a position of a part of the subject in the image to a position of the part of the subject in the space. As another example, the transforming relationship between the first coordinate system applied to the image and the second coordinate system may be used to transform a distance between a part (e.g., a first anatomical location, a second anatomical location) of the subject in the image and a reference position (e.g., the couch, a center, a boundary of the radiation region) to a distance between to the part of the subject in the image and the reference position in the space. In some embodiments, the transforming relationship between the first coordinate system and the second coordinate system may further indicate a corresponding relationship between the couch in different images and positions of the couch in the second coordinate system. For example, the imaging device (e.g., the imaging device 160) may be fixed on the medical radiation device. When the couch is at different positions, the sizes and positions of the couch in the images may be different. Therefore, the corresponding relationship between the different images and the positions of the couch may be determined. That is, the different images may correspond to different positions of the couch. For instance, the farther the distance between the couch and the imaging device, the smaller the couch may be in the image.

In some embodiments, the transforming relationship may be denoted as a transform matrix, a transform function, etc. The transforming relationship may be denoted by the calibration parameters of the imaging device. The calibration parameters may include a focal length, a principal point, a radial distortion, a tangential distortion, a mean reprojection error, a reprojection error, a reprojected point, etc.

In some embodiments, the transforming relationship may be a default setting of the medical system 100. The determination of the transforming relationship may also be referred to as the calibration of the imaging device. The calibration of the imaging device may be performed according to a camera calibration technique, such as a traditional camera calibration technique, an active vision camera calibration technique, a camera self-calibration technique, a zero-distortion camera calibration technique, or the like, or any combination thereof.

In some embodiments, the processing device 120 may update or determine the transforming relationship by obtaining multiple calibration images of the couch acquired by the imaging device when the couch is located at different spatial positions in the second coordinate system. Each of the calibration images may correspond to a spatial position of the couch in the second coordinate system. In some embodiments, the spatial position may be any position within a movable range of the couch in the second coordinate system. For example, the spatial position may include a position of the lowest point of the couch, a position of the highest point of the couch, etc., in the second coordinate system. As another example, the spatial position may include the farthest position of the couch along a negative direction of the Z-axis (e.g., a position closest to the medical radiation device), the farthest position along a positive direction of the Z-axis (e.g., a position farthest from the medical radiation device), etc. In some embodiments, the processing device 120 may sequentially move the couch along the axis or Y-axis to the one or more spatial positions in the second coordinate system. For example, when the spatial position is the lowest point of the couch in the second coordinate system, the processing device 120 may move the couch to the spatial position along the Y-axis. When the spatial position is the farthest position of the couch along the negative direction of the X-axis, the couch may be moved to the spatial position along the X-axis.

In some embodiments, the processing device 120 may determine, based on the multiple calibration images of the couch and the spatial position, the transforming relationship. For example, the processing device 120 may determine a projection position of the couch in each of the calibration images. The processing device 120 may determine the transforming relationship based on the projection positions of the couch and the corresponding spatial position in the second coordinate system using a function fitting. As another example, the processing device 120 may determine the transforming relationship by solving an equation with the transforming relationship as an unknown item and the spatial position and the corresponding projection position as known items. In some embodiments, the processing device 120 may perform a supervised train on a machine learning model based on the multiple calibration images of the couch and the spatial position, so that the machine learning model may be used to determine a spatial position of the couch based on an image.

In some embodiments, the transforming relationship may be updated in response to determining that the imaging device and/or the medical radiation device are varied. For example, after the position of the imaging device, the type of the imaging device, the size of the couch, etc., is varied, the processing device 120 may update the transforming relationship. In some embodiments, the transforming relationship may be updated periodically. For example, the processing device 120 may update the transforming relationship every day, every week, every half month, etc.

In some embodiments, the processing device 120 may obtain the transforming relationship from a storage device, a database, etc. For example, the transforming relationship may be stored in a storage device (e.g., the storage device 130, the storage device 220, the storage 390), a database, etc. The processing device 120 may access the storage device, the database, etc., and retrieve the transforming relationship. In some embodiments, after obtaining the transforming relationship, the processing device 120 may verify the transforming relationship. For example, the processing device 120 may obtain an image and a spatial position of the couch to verify the transforming relationship.

In 720, the processing device 120 (e.g., the determination module 420) may determine, based on a position of a scanning range in the image and the transforming relationship, a starting position of a scanning range and/or an ending position of the scanning range in the second coordinate system.

The scanning range of the subject may refer to a range or a portion of the subject to be scanned. In some embodiments, the processing device 120 may determine the position of the scanning range in the image. The scanning range may be from a starting position corresponding to a first anatomical location of the subject to an ending position corresponding to a second anatomical location of the subject in the image. In some embodiments, the starting position and the ending position may be two locations of the scanning range that have the longest distance from the center of the scanning range along the Z-axis. More descriptions regarding the determination of the position of the scanning range in the image may be found elsewhere in the present disclosure (e.g., operation 530 in FIG. 5 and descriptions thereof).

In some embodiments, the processing device 120 may determine coordinates of the starting position and/or the ending position in the first coordinate system (i.e., in the image). Accordingly, the processing device 120 may determine coordinates of the starting position and/or the ending position in the second coordinate system based on the transforming relationship. For example, the processing device 120 may convert the coordinates of the starting position and/or the ending position in the first coordinate system (i.e., in the image) into the coordinates of the starting position and/or the ending position in the second coordinate system using the transforming relationship.

In 730, the processing device 120 (e.g., the determination module 420) may determine, based on the starting position of the scanning range in the second coordinate system and a position of the radiation region in the second coordinate system, the first distance.

The position of the radiation region may include any position in the radiation region, such as a position of the center of the radiation region on the Z-axis, an edge of the radiation region closest to the couch on the Z-axis, an edge of the radiation region farthest away from the couch on the Z-axis, etc. In some embodiments, the position of the radiation region may be the default setting of the medical system 100, or manually set by a user of the medical system 100 according to different situations. For example, the position of the radiation region may be determined when the radiation device is mounted in the radiation device. In some embodiments, the position of the radiation region may be determined from a layout of the radiation room including the radiation device. The layout of the radiation room may include the structure diagram and position information of different parts of the medical radiation device in the radiation room. Accordingly, the processing device 120 may determine the position in the radiation region in the second coordinate system.

The first distance refers to a distance between the starting position and the position in the radiation region along a long side direction of the couch (i.e., the Z-axis) in the space or the second coordinate system. In some embodiments, the first distance may be a difference between a Z coordinate of the starting position in the second coordinate system and a Z coordinate of the position in the radiation region in the second coordinate system. For example, the processing device 120 may determine the first distance by subtracting the Z coordinate of the position in the radiation region in the second coordinate system from the Z coordinate of the starting position in the second coordinate system.

In 740, the processing device 120 (e.g., the determination module 420) may determine, based on the ending position of the scanning range in the second coordinate system and the position of the radiation region in the second coordinate system, the second distance.

The second distance refers to a distance between the ending position and the position in the radiation region along a long side direction of the couch (i.e., the Z-axis) in the space or the second coordinate system. In some embodiments, the second distance may be a difference between a Z coordinate of the ending position in the second coordinate system and a Z coordinate of the position in the radiation region in the second coordinate system. For example, the processing device 120 may determine the second distance by subtracting the Z coordinate of the position in the radiation region in the second coordinate system from the Z coordinate of the ending position in the second coordinate system.

In 750, the processing device 120 (e.g., the determination module 420) may determine, based on the first position, the first distance, and the second distance, a second position of the couch.

When the couch is located at the second position, the scanning range of the subject may be in the radiation region of the medical radiation device. As used herein, a position of the couch may be represented by a position of a reference point in the couch, such as a center point, a midpoint of an end, a vertex, etc. In some embodiments, the position of the reference point may be denoted by a value of a couch code, etc., of the couch. In some embodiments, the position of the reference point may be denoted by coordinates of the reference point in the second coordinate system. Accordingly, the first position of the couch may be represented by a first position of the reference point in the couch, and the second position of the couch may be represented by a second position of the reference point in the couch.

In some embodiments, the processing device 120 may determine, based on the first distance and/or the second distance, the second position of the couch in a horizontal plane parallel to the couch. For example, if the position of the couch is represented by the position of the center point of the couch, the second position may be in a position range from a position at where the starting position of the scanning range enters the radiation region to a position at where the ending position enters the radiation region. If the first distance and the second distance is from the starting position and the ending position to the edge of the radiation region close to the couch, respectively, when the starting position of the scanning range enters the radiation region, the couch may move from the first position with a moving distance that is same as the first distance; when the ending position of the scanning range enters the radiation region, the couch may move from the first position to the second position with a moving distance that is same as the second distance. When the starting position of the scanning range enters the radiation region, the second position of the couch may be denoted by a first Z coordinate (e.g., a difference by subtracting the first distance from the Z coordinate of the first position in the second coordinate system); when the ending position of the scanning range enters the radiation region, the second position of the couch may be denoted by a second Z coordinate (e.g., a difference by subtracting the second distance from the Z coordinate of the first position in the second coordinate system).

In some embodiments, when the couch is at the second position, the isocenter of the medical radiation device (i.e., the origin of the second coordinate system) may need to coincide with the center of the scanning range to improve the quality of the scan. The processing device 120 may cause the couch to move a distance equal to the first distance and a sum of half of the length of the radiation range. The second position of the couch may be denoted by a Z coordinate (e.g., a difference by subtracting the first distance and the sum of the half of the length of the radiation range from the Z coordinate of the first position in the second coordinate system).

In some embodiments, the processing device 120 may determine, based on depth information, the body thickness of the subject. The image may include depth information. The body thickness of the subject refers to a body length of the subject along the Y-axis (i.e., a direction perpendicular to the surface of the couch). In some embodiments, the depth information of the image may include a distance from a surface of the subject not in contact with the couch (i.e., the upper surface) to the imaging device. For example, if a distance from a point on the lower surface of the subject away from the couch to the imaging device is d1, and a distance from a point on the upper surface of the subject corresponding to the point (i.e., has the same Z coordinate) on the lower surface, the body thickness of the subject may be determined according to the distance d1 and the distance d2. For instance, the body thickness may be a difference between the distance d1 and the distance d2. As another example, the body thickness may be determined by averaging a plurality of distance differences each of which may correspond to a point on the upper surface of the subject and a point on the lower surface of the subject corresponding to the point on the upper surface. Further, the processing device 120 may determine, based on the body thickness of the subject, the second position of the couch in a vertical direction perpendicular to the horizontal plane (i.e., in the Y-axis). For example, if a distance from a center of a cross-section along the X-Y plane to the lower surface (i.e., the rear surface) of the human body is half or one-third of the body thickness and a Z coordinate of the rear surface of the human body is 0, the Z coordinate of the rear surface of the isocenter of the medical radiation device is zero, the processing device 120 may determine the second position of the couch by lowering the couch a portion (e.g., a half, a third, etc.) of the body thickness of the subject. Therefore, the center of the cross-section may be coincident with the isocenter of the medical radiation device, which may improve the quality of the imaging.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, operation 740 may be performed before operation 730. As another example, operation 730 and operation 740 may be performed simultaneously.

Figure 8:
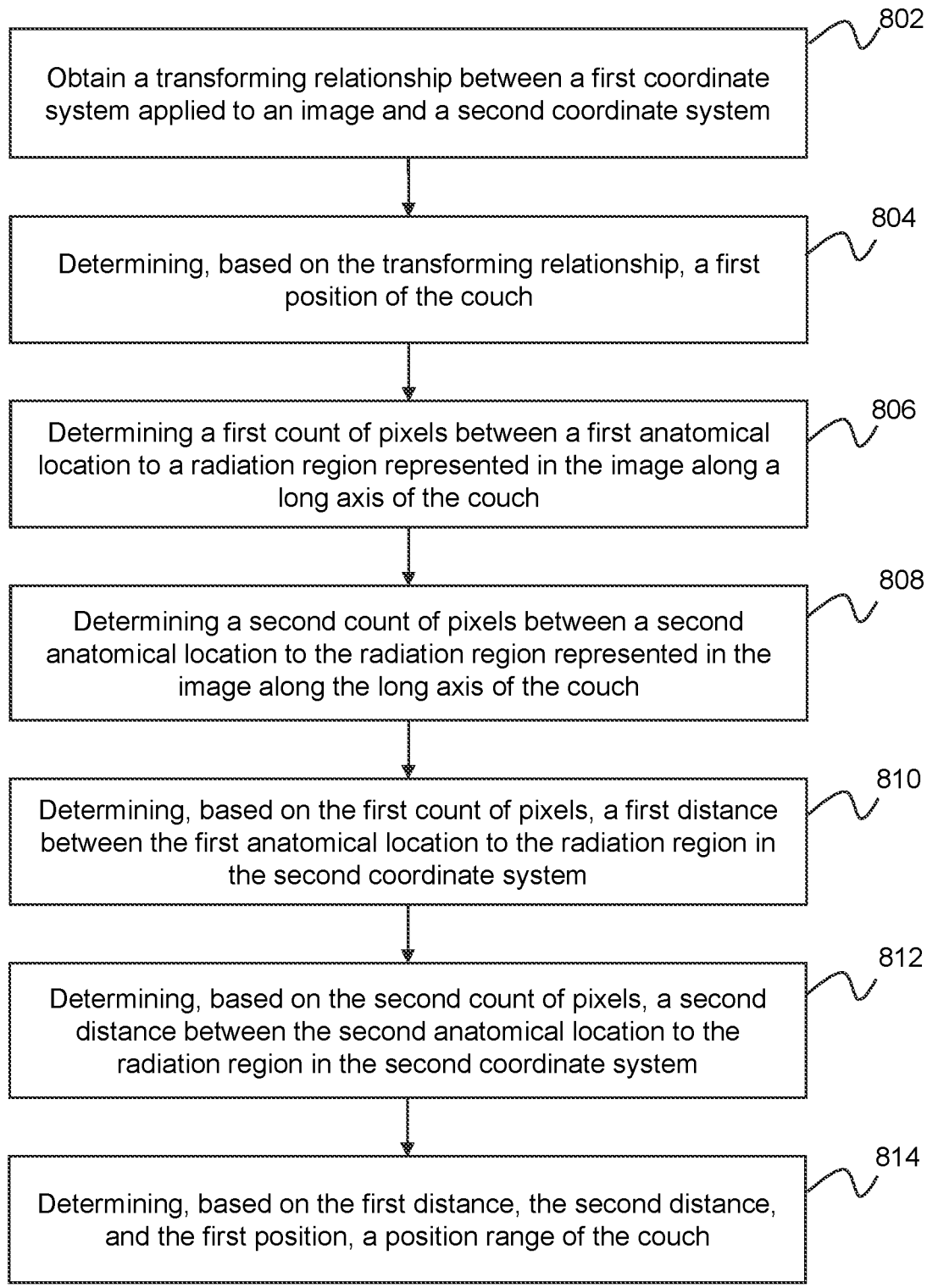
FIG. 8 is a flowchart illustrating another exemplary process for determining a second position of a couch according to some embodiments of the present disclosure.

FIG. 8 is a flowchart illustrating another exemplary process for determining a second position of a couch according to some embodiments of the present disclosure. In some embodiments, process 800 may be implemented in the medical system 100 or the medical system 200 illustrated in FIG. 1. For example, the process 800 may be stored in the storage device 130 and/or the storage (e.g., the storage device 220, the storage 390) as a form of instructions, and invoked and/or executed by the processing device 120 (the processor 210 of the computing device 200 as illustrated in FIG. 2, the CPU 340 of the mobile device 300 as illustrated in FIG. 3). The operations of the illustrated process presented below are intended to be illustrative. In some embodiments, the process 800 may be accomplished with one or more additional operations not described, and/or without one or more of the operations discussed. Additionally, the order in which the operations of the process 800 as illustrated in FIG. 8 and described below is not intended to be limiting. In some embodiments, the operation 540 may be achieved according to the process 800.

In some embodiments, a scanning center point (i.e., isocenter) of a radiation region (e.g., point 690 as shown in FIG. 6) of the medical radiation device may be determined as an origin of the second coordinate system. A long side of the couch may be determined as a Z-axis of the second coordinate system. The direction of the Z-axis may point from the inside to the outside of the radiation region. A plane defined by an X-axis and a Y-axis of the second coordinate system may be perpendicular to the Z-axis. In some embodiments, the X-axis of the second coordinate system may be along the short axis of the couch. A direction perpendicular to a plane defined by the X-axis and the Z-axis may be determined as the Y-axis. In some embodiments, the couch may be caused to move along the X-axis, the Y-axis, and/or the Z-axis. For example, the couch may be moved in and out of the radiation region along the Z-axis, and adjusted along the Y-axis and/or the X-axis. It should be noted that the second coordinate system is merely provided as an exemplary second coordinate system, and not intended to limit the scope of the present disclosure. For example, a radioactive source may be determined as the origin of the second coordinate system. As another example, an origin of the second coordinate system may be a center of the radiation region, or any other point.

In some embodiments, a first coordinate system may be applied to an image acquired by an imaging device (e.g., the imaging device 160) when the couch is at a first position. Merely by way of example, a vertex of the image may be determined as an origin of the first coordinate system. One side of the image may be determined as an X'-axis of the first coordinate system. Another side that is perpendicular to the X'-axis may be determined as a Y'-axis of the first coordinate system. In some embodiments, the X' of the first coordinate system may correspond to the X-axis of the second coordinate system, and the Y'-axis of the first coordinate system may correspond to the Z-axis of the second coordinate system. It should be noted that the first coordinate system is merely provided as an exemplary first coordinate system, and not intended to limit the scope of the present disclosure. For example, a center point of the image may be determined as the origin of the first coordinate system.

In 802, the processing device 120 (e.g., the obtaining module 410) may obtain a transforming relationship between a first coordinate system applied to the image and a second coordinate system.

The transforming relationship between the first coordinate system and the second coordinate system refers to a corresponding relationship between a position of a part of a subject in the image and the position of the part of the subject in the second coordinate system. More descriptions regarding the transforming relationship may be found elsewhere in the present disclosure (e.g., FIG. 7 and descriptions thereof).

In some embodiments, the transforming relationship may further include a transforming ratio. The transforming ratio refers to a ratio of a number of pixels in the image to a corresponding distance in the second coordinate system. For example, if the number of pixels along the X-axis in the image is 500, and a distance along with the Z-axis corresponding to the number of pixels in the second coordinate system is 1 meter, the transforming ratio may be 500 pixels per meter. In some embodiments, the transforming ratio may be related to the transforming relationship. Different transforming relationships may correspond to different transforming ratios. That is, each transforming ratio may correspond to a set of images and couch codes or a transforming relationship. More descriptions for determining the transforming relationship may be found elsewhere in the present disclosure (e.g., operation 710 in FIG. 7).

In some embodiments, the processing device 120 may determine the transforming ratio based on calibration images of the couch acquired at different spatial positions. For example, the processing device 120 may obtain at least one geometric size of the couch in the second coordinate system. The processing device may obtain a count of pixels representing the at least one geometric size in each of the calibration images. For example, the processing device 120 may identify the couch from a calibration image and determine the count of pixels in the first couch representing the at least one geometric size (e.g., the length). The geometric size may refer to a geometric length of the couch, for example, the length, width, and height of the couch. The geometric size of the couch in the second coordinate system refers to an actual size of the couch in the second coordinate system. In some embodiments, the processing device 120 may obtain the geometric size of the couch in the second coordinate system from parameter information of the medical radiation device/couch.

In some embodiments, the processing device 120 may obtain a count of pixels corresponding to the couch along the X-axis (e.g., a width of the couch) in the calibration image. In some embodiments, the processing device 120 may also obtain a count of pixels corresponding to the couch along the Z-axis (e.g., a length of the couch) or the Y-axis in the calibration image.

In some embodiments, the processing device 120 may simultaneously obtain the counts of pixels corresponding to the couch along with multiple directions in the calibration image. For example, the processing device 120 may simultaneously obtain the counts of pixels corresponding to the couch along the X-axis, Y-axis, and Z-axis in the calibration image. As another example, the processing device 120 may simultaneously obtain the counts of pixels corresponding to the couch along with two of the X-axis, Y-axis, or Z-axis in the calibration image.

In some embodiments, the processing device 120 may obtain counts of pixels corresponding to the couch along with multiple directions in the calibration image by traversing the pixels. The processing device 120 may also obtain the count of pixels in another manner, which may not be limited herein.

In some embodiments, the processing device 120 may determine a ratio of the count of pixels to the geometric size of the couch in the second coordinate system. The processing device 120 may designate the ratio of the count of pixels to the geometric size of the couch in the second coordinate system In some embodiments, the processing device 120 may determine the ratio of the count of pixels to the geometric size of the couch in the second coordinate system according to Equation (1):

$$n=S/L, \qquad (1)$$

where n refers to the ratio of the count of pixels to the geometric size of the couch in the second coordinate system; S refers to the count of pixels of the geometric size (e.g., the length, the width, the height) of the couch in the calibration image; and L refers to the geometric size of the couch in the second coordinate system.

In some embodiments, when the counts of pixels of the corresponding geometric size of the couch along with multiple directions (e.g., the X-axis direction, the Z-axis direction) are obtained, S may be a sum of multiple geometric sizes (e.g, the sum of the length and the width), and L may be a sum of geometric sizes of multiple sizes.

In some embodiments, the processing device 120 may obtain a plurality of pairs of spatial position and calibration images and corresponding transforming ratios. Each of the plurality of pairs of spatial position and calibration images may include a calibration image of the couch acquired at a spatial position. Each of the plurality of pairs of spatial position and calibration images may correspond to a transforming ratio. A stepping distance may be spaced between multiple spatial positions, for example, 10 centimeters, 20 centimeters, etc.

When the obtained pairs of spatial positions and calibration images meet a preset requirement, the processing device 120 may determine a transforming relationship. The preset requirement may include that a count of pairs satisfies a preset threshold (e.g., 10 pairs, 20 pairs, etc.), pairs of spatial positions, and calibration images at the spatial positions are acquired (e.g., moving the couch (e.g., from the lowest point to the highest point of the couch, from the farthest position along the positive direction of the Z-axis to the farthest position along the negative direction of the Z-axis, etc.) at the stepping distance, etc.). It should be noted that operations on the couch along the X-axis may be the same as the operations along the Z-axis.

It may be understood that the position of the imaging device may be fixed. When the couch is at different spatial positions, the size of the couch in the calibration images may be different. Therefore, the count of pixels in different calibration images may correspond to different spatial distances. The transforming ratio of the count of pixels of the calibration image to the distance in the second coordinate system may be obtained by calculating the ratio of the count of pixels of the geometric size of the couch in different images to the corresponding geometric size of the couch in the second coordinate system. For example, a transforming ratio of the image in FIG. 6 may be obtained based on a count of pixels on the long side of the couch in the Y'-axis in the image shown in FIG. 6 and an actual length of the long side of the couch. When a new image is obtained, the new image may be matched with one of the calibration images to determine a target calibration image with the same or similar size of the couch as the new image. Accordingly, the transforming ratio corresponding to the image may be obtained.

In some embodiments, the processing device 120 may obtain the transforming relationship and the transforming ratio between the image and coordinates of the position in the second coordinate system by retrieving from an imaging device, a database, a storage device, etc.

In 804, the processing device 120 (e.g., the determination module 420) may determine, based on the transforming relationship, the first position of the couch.

The first position of the couch (also referred to as a current couch code) may indicate coordinates of the couch at the first position in the second coordinate system. In some embodiments, the first position of the couch in the second coordinate system may be represented by a position of a reference point (e.g., a center point, a midpoint of an end, a vertex, a value of couch codes, etc.) of the couch at the first position in the second coordinate system. In some embodiments, the first position may be denoted by coordinates in the second coordinate system. In some embodiments, the first position may be denoted by a couch code.

In some embodiments, the processing device 120 may transform a position (also referred to as projection position) of the couch in the image to the first position of the couch in the second coordinate system based on the transforming relationship, thereby determining the first position (e.g., the current couch code) of the couch. In some embodiments, the processing device 120 may compare the acquired image with multiple calibration images that are used to determining the transforming relationship. The processing device 120 may determine a target calibration image including the couch with the same size and position as the size and position of the couch in the acquired image. The processing device 120 may determine the spatial position (e.g., the couch code) of the couch where the target calibration image of the couch is acquired as the first position of the couch (e.g., the current couch code). As another example, features (e.g., a shape, a texture, a color, a grayscale, etc.) of the image may be extracted. The feature may be used as an input of a function of the transforming relationship obtained by the function fitting to obtain the corresponding couch code. As still another example, the image may be input into a trained machine learning model, and the trained machine learning model may output the corresponding couch code. In some embodiments, the couch may be identified from the image, and the reference point of the couch may be determined from the image, the processing device 120 may convert the position of the reference point in the first coordinate system to the first position of the couch in the second coordinate system using the transforming relationship.

In 806, the processing device 120 (e.g., the determination module 420) may determine a first count of pixels between a first anatomical location to the radiation region represented in the image along a long axis (i.e., the Z-axis) of the couch.

In some embodiments, the processing device 120 may obtain the first count of pixels from the first anatomical location (i.e., the starting position of the scanning range) to the radiation region of the medical radiation device in the image in a traversal manner. For example, the processing device 120 may determine the first anatomical location and the radiation region in the image using a trained machine learning model. As another example, the processing device 120 may determine the first anatomical location and the radiation region in the image using a template matching algorithm. More descriptions regarding the determination of the first anatomical location and the radiation region in the image may be found elsewhere in the present disclosure (e.g., FIG. 7 and descriptions thereof).

In some embodiments, the first count of pixels may include the count of pixels from the first anatomical location to an isocenter of the radiation region in the image along a direction (e.g., the Y'-axis). Alternatively, the first count of pixels may include the count of pixels from the first anatomical location to an edge of the radiation region close to the couch (indicated by the dashed line 610 in FIG. 6) or an edge of the radiation region far away from the couch along a direction (e.g., the Y'-axis).

In 808, the processing device 120 (e.g., the determination module 420) may determine a second count of pixels between the second anatomical location to the radiation region represented in the image along the long axis (i.e., the Z-axis) of the couch.

In some embodiments, the processing device 120 may obtain the second count of pixels from the second anatomical location to the radiation region of the medical radiation device in the image in a traversal manner. For example, the processing device 120 may determine the second anatomical location and the radiation region in the image using a trained machine learning model. As another example, the processing device 120 may determine the second anatomical location and the radiation region in the image using a template matching algorithm. More descriptions regarding the determination of the first anatomical location and the radiation region in the image may be found elsewhere in the present disclosure (e.g., FIG. 7 and descriptions thereof).

In some embodiments, the second count of pixels may include the count of pixels from the second anatomical location to the isocenter of the radiation region in the image along a direction (e.g., the Y'-axis). Alternatively, the second count of pixels may include the count of pixels from the second anatomical location to the edge of the radiation region close to the couch (indicated by the dashed line 610 in FIG. 6) or the edge of the radiation region far away from the couch along a direction (e.g., the Y'-axis).

In 810, the processing device 120 (e.g., the determination module 420) may determine, based on the first count of pixels, a first distance between the first anatomical location to the radiation region in the second coordinate system.

In some embodiments, the processing device 120 may perform a scaling operation based on the first count of pixels and the transforming ratio to obtain the first distance between the first anatomical location to the radiation region in the second coordinate system. For example, if the first count of pixels is 500 and the transforming ratio is 500 pixels per meter, the processing device 120 may determine that the first distance is 1 meter. The transforming ratio may be determined based on the first position of the couch. For example, the processing device 120 may retrieve a corresponding transforming ratio from a storage device based on the first position of the couch.

In 812, the processing device 120 (e.g., the determination module 420) may determine, based on the second count of pixels, a second distance between the second anatomical location to the radiation region in the second coordinate system.

In some embodiments, the processing device 120 may perform a scaling operation based on the second count of pixels and the transforming ratio to obtain the second distance between the second anatomical location to the radiation region in the second coordinate system. The transforming ratio may be determined based on the first position of the couch. For example, the processing device 120 may retrieve a corresponding transforming ratio from a storage device based on the first position of the couch. More descriptions regarding the determination of the second distance may be found elsewhere in the present disclosure (e.g., operation 810 in FIG. 8 and descriptions thereof).

In 814, the processing device 120 (e.g., the determination module 420) may determine, based on the first distance, the second distance, and the first position, a position range of the couch.

The position range (also referred to as a target couch code) of the couch may refer to a coordinate range of the couch in the second coordinate system from a position at where the first anatomical location is transferred to the radiation region a position at where the second anatomical location is transferred to the radiation region of the medical radiation device. The coordinates (or couch code) of the couch in the second coordinate system may be expressed by position coordinates of a reference point of the couch in the second coordinate system, such as position coordinates of a center point 660 of the couch in an X-Z plane or other any point (e.g., a point 670, a point 680, etc.) as shown in FIG. 6.

The radiation region of the medical radiation device may refer to a range covered by the radiation beams emitted by a radioactive source of the medical radiation device, or a region corresponding to a detector of the medical radiation device along the X-axis. In the second coordinate system, the radiation region of the medical radiation device may correspond to a fixed coordinate range. The couch may be caused to move into the radiation region. In some embodiments, the processing device 120 may determine a section of the couch that corresponds to the scanning range of the subject, i.e., where the scanning range of the subject is located on the couch. By moving the section of the couch into the radiation region, the scanning range of the subject may be moved into the radiation region of the medical radiation device. For example, a first edge (i.e., the front edge) of the section of the couch may correspond to the starting position of the scanning range and a second edge of the section of the couch may correspond to the ending position of the scanning range.

In some embodiments, when the front edge of the section of the couch (or the starting position of the scanning range) enters the radiation region, the couch may include corresponding first coordinates (or a first couch code) in the second coordinate system. When the section of the couch passes through the radiation region and a trailing edge of the section (or the ending position of the scanning range) leaves the radiation region, the couch may include corresponding second coordinates (or a second couch code) in the second coordinate system. The range between the first coordinates and the second coordinates may be the position range (i.e., the second position) of the couch for scanning the subject on the couch.

In some embodiments, when a trailing edge of the section of the couch (or the ending position of the scanning range) enters the radiation region, the couch may include corresponding first coordinates (or a first couch code) in the second coordinate system; after the ending position of the scanning range enters the radiation region when the front edge of the section (or the starting position of the scanning range) leaves the radiation region, the couch may include corresponding second coordinates (or a second couch code) in the second coordinate system. The range between the first coordinates and the second coordinates may be the position range (i.e., the second position) of the couch for scanning the subject on the couch.

In some embodiments, after the first distance and the second distance are determined, the processing device 120 may determine, based on the first distance, the second distance, and the first position, the position range of the couch.

As shown in FIG. 6, in some embodiments, an edge (indicated as the dashed edge of 610 in FIG. 6) on a side close to the couch (e.g., a right side of the scanning center as shown in FIG. 6) of the radiation region may be used to describe the position of the radiation region in the image or the second coordinate system. The reference point 670 on the couch may be used to describe the position of the couch in the image or the second coordinate system. For example, Z-axis coordinates of the radiation region in the image may be within a range from P1 to P2. The starting position of the scanning range may be denoted as A1 and the ending position of the scanning range may be denoted as A2 when the couch is located at the first position R1. A minimum distance that the starting position of the scanning range A1 enters the radiation region along the Z-axis (i.e., a distance between positions A1 and P1) may be a first distance D1. A minimum distance that the ending position of the scanning range A2 enters the radiation region along the Z-axis (i.e., a distance between the positions A2 and P1) may be a second distance D2. Since the starting position of the scanning range A1 may enter the radiation region before the ending position of the scanning range A2, the second distance D2 may be greater than the first distance D1. Therefore, when the couch is moved with the second distance D2, the scanning range between the starting position of the scanning range A1 and the ending position of the scanning range A2 may be located in the radiation region. If the couch continues to be moved, the starting position of the scanning range A1 may move out of the radiation region from the other side of the radiation region (e.g., P2).

In some embodiments, the position range of the couch may be from a position of the couch when the ending position of the scanning range A2 enters the radiation source to a position of the couch when the starting position of the scanning range A1 leaves the radiation region. If the direction of the Z-axis points from the inside to outside of the radiation region (as shown in FIG. 6), the position (e.g., the first coordinates or first couch code) of the couch when the ending position of the scanning range A2 enters the radiation source may be equal to a difference between the first position R1 and a first moving distance (i.e., the second distance D2) of the couch from the first position R1 to the position when the ending position of the scanning range A2 enters the radiation source; the position (e.g, the second coordinates or second couch code) of the couch when the starting position of the scanning range A1 leaves the radiation region may be equal to a difference between the first position R1 and a second moving distance from the first position R1 to the position when the starting position of the scanning range A1 leaves the radiation region. Moving distances of the couch in the second coordinate system may be determined based on the first distance D1 and the second distance D2. For example, the first moving distance D1 may be equal to the second distance D2. The second moving distance D2 may be equal to the sum of the first distance D1 and the length of the radiation region (i.e., P2-P1).

In some embodiments, the position range of the couch may be from a position of the couch when the starting position of the scanning range A1 enters the radiation source to a position of the couch when the ending position of the scanning range A2 enters the radiation region. If the direction of the Z-axis points from the inside to outside of the radiation region (as shown in FIG. 6), the position (e.g., the first coordinates or first couch code) of the couch when the starting position of the scanning range A1 enters the radiation source may be equal to a difference between a first moving distance of the couch from the first position R1 to the position when the starting position of the scanning range A1 enters the radiation source and the first position R1; the position (e.g., the second coordinates or second couch code) of the couch when the ending position of the scanning range A2 enters the radiation region may be equal to a difference between a second moving distance from the first position R1 to the position when the ending position of the scanning range A2 enters the radiation region and the first position R1. The first moving distance D1 may be equal to the first distance S1. The second moving distance D2 may be equal to the second distance S2.

In some embodiments, the current couch code (i.e., the first position R1) corresponding to the current image (i.e., the image) may be determined based on the transforming relationship between the first coordinate system and the second coordinate system. When the couch moves by the distance D1 based on the current couch code (i.e., the first position R1), coordinates of the couch in the second coordinate system may be the first couch code. When the couch moves by the distance D2 based on the current couch code, coordinates of the couch in the second coordinate system may be the second couch code. When the couch moves between the first couch code and the second couch code, the scanning region between the first anatomical location and the second anatomical location of the subject may be within the radiation region. Therefore, the coordinate range between the first couch code and the second couch code may be the position range of the couch.

In some embodiments, the processing device 120 may determine, based on the first distance and the current couch code (corresponding to the first position of the couch), the first couch code. The first couch code may refer to a couch code of the couch in the second coordinate system when the starting position corresponding to the first anatomical location of the subject on the couch enters the radiation region (e.g., the edge P1 on the side of the radiation region close to the couch). In some embodiments, the processing device 120 may determine, based on the second distance and the current couch code (corresponding to the first position of the couch), the first couch code. The second couch code may refer to a couch code of the couch in the second coordinate system when the ending position corresponding to the second anatomical location of the subject on the couch enters the radiation region (e.g., the edge P1 on the side of the radiation region close to the couch).

In some embodiments, the Z coordinate of the current couch code may be shifted positively or negatively based on the first distance to obtain the Z coordinate of the first couch code. For example, if the Z coordinate of the current couch code is 2 and the couch is positively shifted by one unit coordinate, the Z coordinate of the first couch code may be determined to be 3. Alternatively, if the Z coordinate of the current couch code is 2 and the couch is negatively shifted by one unit coordinate, the Z coordinate of the first couch code may be determined to be 1. In some embodiments, if there is no need to move the couch in the Y-axis and the X-axis, the processing device 120 may subtract the first distance from the Z coordinate of the current couch code to obtain the first couch code. In some embodiments, the Z coordinate of the current couch code may be shifted positively or negatively based on the second distance to obtain the Z coordinate of the second couch code. For example, the processing device 120 may subtract the second distance from the Z coordinate of the current couch code to obtain the second couch code.

In some embodiments, the image may further include depth information. The processing device 120 may determine the body thickness of the subject based on the image. More descriptions regarding the body thickness may be found elsewhere in the present disclosure (e.g., FIG. 7 and descriptions thereof). Accordingly, the processing device 120 may further adjust the Y coordinate based on the adjustment of the x coordinate value to obtain the first couch code. For example, the processing device 120 may adjust the Y coordinate of the current couch code based on a portion of the body thickness to reduce the distance between a center of a cross-section of the subject and the scanning center of the medical radiation device along the Y-axis to obtain the Y coordinate of the first couch code.

Taking the human body as an example, a plane parallel to a Y-Z plane that passes through the center of the eyebrow of the human body to divide the human body into two may be a sagittal plane. A plane parallel to an X-Z plane that divides the human body into upper and lower sides from a side of the human body may be a coronal plane. A plane parallel to an X-Y plane that is perpendicular to the coronal plane and the sagittal plane, respectively, may be a cross-section (a horizontal plane). In some embodiments, the center of the cross-section may be a center of gravity, a center of mass, a center of symmetry, etc. In some embodiments, half or one-third of the body thickness may be considered as a distance d from the center of the cross-section to the rear surface of the human body.

In some embodiments, the scanning center may be a center inherent to the medical radiation device. For example, the scanning center may include a rotation center of the radioactive source (the center of the radiation region), a geometric center of a gantry, etc. The center of the cross-section may be coincident with the center of the scanning region during the scanning, which may improve the quality of the imaging.

In some embodiments, the processing device 120 may move the couch along the Y-axis to move the Y coordinate of the center of the cross-section of the subject to the scanning center of the medical radiation device along the Z-axis. For example, (0-d) may be used as the Y coordinate of the first couch code.

Therefore, the X-axis coordinate and the Y-axis coordinate of the first couch code may be determined. Since the positioning of the couch does not involve a movement along the Z-axis, the Z coordinate of the couch may be a fixed value, which may be obtained when the second coordinate system is established. Therefore, the X, Y, and Z coordinates of the first couch code may be determined.

It should be noted that when the Z coordinate of the couch needs to be determined, the operation of determining the X coordinate may be used.

The second couch code may be determined through an operation as same as the operation of determining the first couch code, which may not be repeated.

In some embodiments, the processing device 120 may determine a position range between the first couch code and the second couch code as the position range of the couch.

It should be noted that the above description is merely provided for illustration, and not intended to limit the scope of the present disclosure. For persons having ordinary skills in the art, multiple variations and modifications may be made under the teachings of the present disclosure. However, those variations and modifications do not depart from the scope of the present disclosure. For example, operation 808 may be performed before operation 806. As another example, operation 806 and operation 808 may be performed simultaneously.

Figure 9:
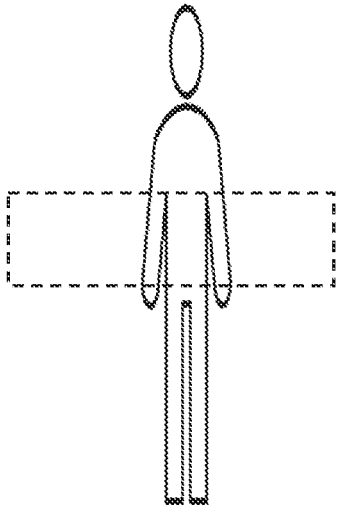
FIG. 9 is a schematic diagram illustrating an exemplary user interface according to some embodiments of the present disclosure.

FIG. 9 is a schematic diagram illustrating an exemplary user interface according to some embodiments of the present disclosure. The user interface may be used for configuring a scanning protocol (or a portion of the scanning plan).

As shown in FIG. 9, the user interface may include multiple operating controls. Each of the multiple operating controls may correspond to one of the multiple anatomical locations. A left block of the user interface may include protocol parameters (e.g., a label configured to input identity information of a subject, a perspective (e.g., a frontal direction, a lateral direction, and a dual direction), a starting position, an ending position, a length, a height, a scanning time, a field of view (FOV), a scanning direction (e.g., head to foot and foot to hand), an auxiliary function (e.g., an auto voice, an intelligent workflow, etc.), etc.) of the scanning protocol configuration. A user may visually input or adjust the protocol parameters to configure the scanning protocol. For example, the user may visually operate the multiple operating controls to configure a starting position and an ending position of a scanning range in the scanning protocol. As another example, the user may use a button to select an anatomical location corresponding to the button to determine the starting position and the ending position. A right block of the user interface may include a human anatomical structure map that includes the multiple anatomical locations and a dashed frame represented a radiation region of a medical radiation device. The user may visually determine the scanning protocol by selecting one or more anatomical locations in the anatomical structure and/or dragging the dashed frame.

It should be noted that the above description is merely provided for illustration, and not intended to limit the scope of the present disclosure. For persons having ordinary skills in the art, multiple variations and modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended for those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including a subject oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

What is claimed is:

1. A system, comprising:
   at least one storage device including a set of instructions; and
   at least one processor configured to communicate with the at least one storage device, wherein when executing the set of instructions, the at least one processor is configured to direct the system to perform operations including:
   obtaining data associated with a scanning range of a subject, wherein the scanning range of the subject includes to a first anatomical location of the subject and a second anatomical location of the subject;
   obtaining an image of the subject on a couch of a medical radiation device, the image being acquired by an imaging device when the couch is at a first position;
   determining, based on the data associated with the scanning range of the subject, a position of the scanning range of the subject in the image; and
   causing, based on the position of the scanning range in the image, the couch to move to a second position, including:
   obtaining a transforming relationship between a first coordinate system applied to the image and a second coordinate system, wherein the second coordinate system is a spatial coordinate system which is established based on a position of the medical radiation device, the transforming relationship including a transforming ratio of a number of pixels in the image to a corresponding distance in the second coordinate system;
   determining, based on the transforming relationship, the first position of the couch in the second coordinate system;
   determining, based on the position of the scanning range in the image, a first count of pixels from the first anatomical location to a radiation region of the medical radiation device in the image along a long axis of the couch;
   determining, based on the position of the scanning range in the image, a second count of pixels from the second anatomical location to the radiation region of the medical radiation device in the image along the long axis of the couch;
   determining, based on the first count of pixels, a first distance from the first anatomical location to the radiation region in the second coordinate system;
   determining, based on the second count of pixels, a second distance between the second anatomical location to the radiation region in the second coordinate system; and
   determining, based on the first distance, the second distance, the first position, and the transforming ratio, the second position of the couch.

2. The system of claim 1, wherein the obtaining data associated with the scanning range of the subject includes:
   obtaining the data associated with the scanning range of the subject from a scanning plan; or
   obtaining the data associated with the scanning range of the subject according to an input of a user.

3. The system of claim 1, wherein the obtaining data associated with the scanning range of the subject includes:
   causing a display device to present a user interface including multiple operating controls; and
   determining the data associated with the scanning range of the subject in response to receiving an input of a user through the multiple operating controls.

4. The system of claim 3, wherein the user interface is used to configure a scanning protocol, and includes a human anatomical structure map that includes multiple anatomical locations each of which corresponds to one of the multiple operating controls,
   and the determining the data associated with the scanning range of the subject in response to receiving an input of the user through the multiple operating controls includes:
   receiving an operation of the user on one or more of the multiple operating controls;
   determining, based on the operation of the user on one or more of the multiple operating controls, a configuration of the scanning range in the scanning protocol; and
   determining, based on the configuration of the scanning range, the data associated with the scanning range of the subject.

5. The system of claim 1, wherein the image is acquired from an overlook view of the subject by the imaging device that is located above the couch.

6. The system of claim 1, wherein the determining a position of the scanning range of the subject in the image includes:
   determining the position of the scanning range of the subject in the image by inputting the data associated with the scanning range and the image into a trained machine learning model.

7. The system of claim 1, wherein the causing, based on the first distance, the second distance, the first position, and the transforming ratio, the second position of the couch includes:
   determining, based on the depth information, a body thickness of the subject;

determining, based on the first distance, the second distance, the first position, and the transforming ratio, the second position of the couch in a horizontal plane parallel to the couch;

determining, based on the body thickness of the subject, the second position of the couch in a vertical direction perpendicular to the horizontal plane.

8. The system of claim 1, wherein the control platform is configured to:

obtaining multiple calibration images of the couch acquired by the imaging device, each of the calibration images corresponding to a spatial position of the couch in the second coordinate system; and determining, based on the multiple calibration images of the couch and the spatial position, the transforming relationship.

9. The system of claim 1, wherein the operations further include:

outputting, through a user interface, the second position to a terminal of a user;

receiving an adjustment instruction for adjusting the second position provided by the user through the user interface; and causing, based on the adjustment instruction, the couch to move.

10. A method implemented on a computing device including at least one processor and storage medium, comprising:

obtaining data associated with a scanning range of a subject, wherein the scanning range of the subject includes a first anatomical location of the subject and a second anatomical location of the subject;

obtaining an image of the subject on a couch of a medical radiation device, the image being acquired by an imaging device when the couch is at a first position;

determining, based on the data associated with the scanning range of the subject, a position of the scanning range of the subject in the image; and causing, based on the position of the scanning range in the image, the couch to move to a second position, including:

obtaining a transforming relationship between a first coordinate system applied to the image and a second coordinate system, wherein the second coordinate system is a spatial coordinate system which is established based on a position of the medical radiation device, the transforming relationship including a transforming ratio of a number of pixels in the image to a corresponding distance in the second coordinate system;

determining, based on the transforming relationship, the first position of the couch in the second coordinate system;

determining, based on the position of the scanning range in the image, a first count of pixels from the first anatomical location to a radiation region of the medical radiation device in the image along a long axis of the couch;

determining, based on the position of the scanning range in the image, a second count of pixels from the second anatomical location to the radiation region of the medical radiation device in the image along the long axis of the couch;

determining, based on the first count of pixels, a first distance from the first anatomical location to the radiation region in the second coordinate system;

determining, based on the second count of pixels, a second distance between the second anatomical location to the radiation region in the second coordinate system; and determining, based on the first distance, the second distance, the first position, and the transforming ratio, the second position of the couch.

11. The method of claim 10, wherein the obtaining data associated with the scanning range of the subject includes:

obtaining the data associated with the scanning range of the subject from a scanning plan; or obtaining the data associated with the scanning range of the subject according to an input of a user.

12. The method of claim 10, wherein the obtaining data associated with the scanning range of the subject includes:

causing a display device to present a user interface including multiple operating controls; and determining the data associated with the scanning range of the subject in response to receiving an input of a user through the multiple operating controls.

13. The method of claim 12, wherein the user interface is used to configure a scanning protocol, and includes a human anatomical structure map that includes multiple anatomical locations each of which corresponds to one of the multiple operating controls, and the determining the data associated with the scanning range of the subject in response to receiving an input of the user through the multiple operating controls includes:

receiving an operation of the user on one or more of the multiple operating controls;

determining, based on the operation of the user on one or more of the multiple operating controls, a configuration of the scanning range in the scanning protocol; and determining, based on the configuration of the scanning range, the data associated with the scanning range of the subject.

14. The method of claim 10, wherein the determining a position of the scanning range of the subject in the image includes:

determining the position of the scanning range of the subject by inputting data associated with the scanning range into the image using a trained machine learning model.

15. A non-transitory computer readable medium, comprising executable instructions that, when executed by at least one processor, direct the at least one processor to perform a method, the method comprising:

obtaining data associated with a scanning range of a subject, wherein the scanning range of the subject-includes a first anatomical location of the subject and a second anatomical location of the subject;

obtaining an image of the subject on a couch of a medical radiation device, the image being acquired by an imaging device when the couch is at a first position;

determining, based on the data associated with the scanning range of the subject, a position of the scanning range of the subject in the image; and causing, based on the position of the scanning range in the image, the couch to move to a second position, including:

obtaining a transforming relationship between a first coordinate system applied to the image and a second coordinate system, wherein the second coordinate system is a spatial coordinate system which is established based on a position of the medical radiation device, the transforming relationship including a transforming ratio of a number of pixels in the image to a corresponding distance in the second coordinate system;

determining, based on the transforming relationship, the first position of the couch in the second coordinate system;

determining, based on the position of the scanning range in the image, a first count of pixels from the first anatomical location to a radiation region of the medical radiation device in the image along a long axis of the couch;

determining, based on the position of the scanning range in the image, a second count of pixels from the second anatomical location to the radiation region of the medical radiation device in the image along the long axis of the couch;

determining, based on the first count of pixels, a first distance from the first anatomical location to the radiation region in the second coordinate system;

determining, based on the second count of pixels, a second distance between the second anatomical location to the radiation region in the second coordinate system; and determining, based on the first distance, the second distance, the first position, and the transforming ratio, the second position of the couch.

16. The system of claim 1, wherein causing, based on the position of the scanning range in the image, the couch to move to a second position includes:

determining whether a length of the scanning range is greater than a length of the radiation region;

in response to determining that the length of the scanning range is greater than the length of the radiation region, determining that the second position including a first position range from a position that a starting position of the scanning range enters the radiation region to a position that an ending position of the scanning range enters the radiation region; and in response to determining that the length of the scanning range is less than or equal to the length of the radiation region, determining that the second position including a position in a second position range from a position that the ending position of the scanning range enters the radiation region to a position that the starting position of the scanning range leaves the radiation region.

17. The system of claim 16, wherein in response to determining that the length of the scanning range is greater than the length of the radiation region, determining that the second position including a first position range from a position that a starting position of the scanning range enters the radiation region to a position that an ending position of the scanning range enters the radiation region includes:

determining a distance range from a minimum moving distance that the starting position of the scanning range enters the radiation region to a maximum moving distance that the ending position of the scanning range enters the radiation region; and determining the first position range based on the distance range.

18. The system of claim 16, wherein in response to determining that the length of the scanning range is less than or equal to the length of the radiation region, determining that the second position including a position in a second position range from a position that the ending position of the scanning range enters the radiation region to a position that the starting position of the scanning range leaves the radiation region includes:

determining a distance range from a minimum moving distance that the ending position of the scanning range enters the radiation region to a maximum moving distance that the starting position of the scanning range leaves the radiation region; and determining the second position range based on the distance range.

19. The system of claim 8, wherein determining, based on the multiple calibration images of the couch and the spatial position, the transforming relationship includes:

determining a projection position of the couch in each of the calibration images; and determining the transforming relationship based on the projection position of the couch in each of the calibration image and the spatial position in the second coordinate system using a function fitting.

20. The system of claim 1, wherein the obtaining a transforming relationship between a first coordinate system applied to the image and a second coordinate system includes:

obtaining a plurality of calibration images of the couch, each of the plurality of calibration images being acquired when the couch is at the first position;

for each of the plurality of calibration images of the couch, determining a count of pixels corresponding to the couch in the calibration image; and determining a transforming ratio based on the count of pixels and a geometric size of the couch in the second coordinate system.

* * * * *